United States Patent
Jin et al.

(10) Patent No.: US 11,555,060 B2
(45) Date of Patent: Jan. 17, 2023

(54) QTY FC FUSION WATER SOLUBLE RECEPTOR PROTEINS

(71) Applicants: Massachusetts Institute of Technology, Cambridge, MA (US); Avalon GloboCare Corp., Freehold, NJ (US)

(72) Inventors: David Jin, Staten Island, NY (US); Rui Qing, Somerville, MA (US); Shuguang Zhang, Cambridge, MA (US)

(73) Assignees: Avalon GloboCare Corp., Freehold, NJ (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/210,837

(22) Filed: Mar. 24, 2021

(65) Prior Publication Data
US 2021/0300993 A1    Sep. 30, 2021

Related U.S. Application Data

(60) Provisional application No. 62/994,433, filed on Mar. 25, 2020.

(51) Int. Cl.
| | | |
|---|---|---|
| C07K 14/715 | (2006.01) | |
| A61K 35/17 | (2015.01) | |
| A61K 38/00 | (2006.01) | |

(52) U.S. Cl.
CPC .......... *C07K 14/7155* (2013.01); *A61K 35/17* (2013.01); *C07K 14/7156* (2013.01); *A61K 38/00* (2013.01); *C07K 2317/52* (2013.01); *C07K 2319/03* (2013.01); *C07K 2319/30* (2013.01)

(58) Field of Classification Search
CPC .... A61K 38/00; A61K 47/68; C07K 2319/03; C07K 2319/30; C07K 2317/52; C07K 14/7155
See application file for complete search history.

(56) References Cited

U.S. PATENT DOCUMENTS

| | | | | |
|---|---|---|---|---|
| 8,637,452 B2 * | 1/2014 | Zhang | .................. | A61K 38/177 514/1.7 |
| 2003/0078220 A1 * | 4/2003 | Chew | ................. | C12N 15/8509 514/44 R |
| 2018/0118806 A1 | 5/2018 | Zhang | | |
| 2019/0353654 A1 * | 11/2019 | Zhang | ............... | C07K 14/7158 |

OTHER PUBLICATIONS

Brown, S.J., et al. Expression and ligand binding assays of soluble cytokine receptor-immunoglobulin fusion proteins. Protein Expression and Purification, 1998, 14:120-124.*

Czajkowsky, D.M., et al. Fc-fusion proteins: new developments and future perspectives. EMBO Molecular Medicine, 2012, 4:1015-1028.*
Dinarello, C.A. Biologic basis for interleukin-1 in disease. Blood, 1996, 87(6):2095-2147.*
Hao, S., et al. QTY code-designed water-soluble Fc-fusion cytokine receptor bind to their respecctive ligands. QRB Discovery, 1:e4, p. 1-9.*
Janssens, R., et al. Pathological roles of the homeostatic chemokine CXCL12. Cytokine and Growth Factor Reviews, 2018, 44:51-68.*
Levin, D., et al. Fc fusion as a platform technology: potential for modulating immunogenicity. Trends in Biotechnology, 2015, 33(1):27-34.*
Tseng, D., et al. Targeting SDF-1/CXCR4 to inhibit tumour vasculature for treatment of glioblastomas. British Journal of Cancer, 2011, 104:1805-1809.*
Wenzel, S.E., et al., IL4Ra mutations are associated with asthma exacerbations and mast cell/IgE expression. Am. J. Respir. Crit. Care Med., 2007, 175:570-576.*
Zhang, S., et al. QTY code enables design of detergent-free chemokine receptors that retain ligand-binding activities. Proc. Natl. Acad. Sci. USA, 2018, 115(37):E8652-E8659).*
GenBank Accession No. X52425 (human IL-4-R mRNA for the interleukin 4 receptor), downloaded Jun. 19, 2021.*
Baybutt, T. R. et al., "Advances in chimeric antigen receptor T-Cell therapies for solid tumors", Clinical Pharmacology & Therapeutics, 105(1), 2019, 71-78.
Caccuri, F. et al., "HIV-1 matrix protein p17 promotes angiogenesis via chemokine receptors CXCR1 and CXCR2", Proceedings of the Proc Natl Acad Sci USA, 109(36), Sep. 4, 2012, 14580-14585.
Celada, A. et al., "Demonstration and partial characterization of the interferon-gamma-receptor on human mononuclear phagocytes", Journal of Clinical Investigation, 76(6), 1985, 2196-2205.
Czajkowsky, D.M., et al., "Fc-Fusion Proteins: New Developments and Future Perspectives," EMBO Molecular Medicine, 4, pp. 1015-1028 (2012).
De Jong, M. D. et al., "Fatal outcome of human influenza A (H5N1) is associated with high viral load and hypercytokinemia", Nature Medicine, 12(10), Oct. 2006, 1203-1207.
Eberhardson, M. et al., "Randomised, double-blind, placebo-controlled trial of CCR9-targeted leukapheresis treatment of ulcerative colitis patients", Journal of Crohns & Colitis, 11(5), doi:10.1093/ecco-jcc/jjw196, 2017, 534-542.
Hu, Y. et al., "Specific killing of CCR9 high-expressing acute T lymphocytic leukemia cells by CCL25 fused with PE38 toxin", Leukemia Research, 35(9), 2011, 1254-1260.
Huang, C. et al., "Clinical features of patients infected with 2019 novel coronavirus in Wuhan, China", Lancet, 395(10223), Feb. 15, 2020, 496-496.
Ittershagen, S. et al., "Industry's giant leap into cellular therapy: catalyzing chimeric antigen receptor T cell (CAR-T) immunotherapy", Current Hematologic Malignancy Reports, 14(1), Jan. 21, 2019, 47-55.
Jain, M. D. et al., "Concise Review: Emerging principles from the clinical application of chimeric antigen receptor t cell therapies for B cell malignancies", Stem Cells, 36(1), 2018, 36-44.
Jerabek-Willemsen, M. et al., "MicroScale thermophoresis: interaction analysis and beyond", Journal of Molecular Structure, 1077, http://dx.doi.org/10.1016/j.molstruc.2014.03.009, Mar. 16, 2014, 101-113.

(Continued)

Primary Examiner — Prema M Mertz
(74) Attorney, Agent, or Firm — Elmore Patent Law Group, P.C.; Carolyn Elmore

(57) ABSTRACT

The present invention is directed to QTY Fc receptor fusion proteins, methods for the preparation thereof and methods of use thereof.

7 Claims, 3 Drawing Sheets

Specification includes a Sequence Listing.

(56) References Cited

OTHER PUBLICATIONS

Kwon, H. R., "Study of the structure and function of CXC chemokine receptor 2", Master's Thesis, University of Tennessee, 2010.
Laporte, S. L. et al., "Molecular and structural basis of cytokine receptor pleiotropy in the interleukin-4/13 system", Cell, 132(2), Jan. 25, 2008, 259-272.
Mekhaiel, D..N. A. et al., "Polymeric human Fc-fusion proteins with modified effector functions", Scientific Reports, 1(124), DOI: 10.1038/srep00124, Oct. 19, 2011, 1-11.
Mikulecky, P. et al., "Increasing affinity of interferon-gamma receptor 1 to interferon-gamma by computer-aided design", Biomed Research International, vol. 2013, Article ID 752514, http://dx.doi.org/10.1155/2013/752514, Oct. 2, 2013, 12 pgs.
Qing, R. et al., "QTY code designed thermostable and water-soluble chimeric chemokine receptors with tunable ligand affinity", Proc Natl Acad Sci USA,, 116(51), www.pnas.org/cgi/doi/10.1073/pnas.1909026116, Nov. 27, 2019, 25668-25676.
Rajarathnam, K. et al., "Probing receptor binding activity of interleukin-8 dimer using a disulfide trap", Biochemistry, 45(25), Jun. 3, 2006, 7882-7888.
Richter, D. et al., "Ligand-induced type II interleukin-4 receptor dimers are sustained by rapid re-association within plasma membrane microcompartments", Nature Communications, 8, No. 15976, DOI: 10.1038/ncomms15976, Jul. 14, 2017, 1-15.
Savarin, C. et al., "Fine Tuning the Cytokine Storm by IFN and IL-10 Following Neurotropic Coronavirus Encephalomyelitis", Frontiers in Immunology, 9, 3022, doi: 10.3389/fimmu.2018.03022, Dec. 20, 2018, 1-8.
Shimabukuro-Vornhagen, A. et al., "Cytokine release syndrome", Journal for Immunotherapy of Cancer, 6(56), https://doi.org/10.1186/s40425-018-0343-9, Jun. 15, 2018, 1-14.
Somovilla-Crespo, B. et al., "92R monoclonal antibody inhibits human CCR9(+) leukemia cells growth in NSG mice xenografts", Frontiers in Immunology, 9(77), doi: 10.3389/fimmu.2018.00077, Jan. 29, 2018, 1-12.
Sonnhammer, E. L. et al., "A hidden Markov model for predicting transmembrane helices in protein sequences", In J. Glasgow et al., eds., Proc. Sixth Int. Conf. on Intelligent Systems for Molecular Biology, 175-182. AAAI Press, 1998, 1-8.
Srivastava, S. et al., "Engineering CAR-T cells: Design concepts", Trends in Immunology, 36(8), doi:10.1016/j.it.2015.06.004, Aug. 2015, 494-502.
Suzuki, T. et al., "Importance of Neonatal FcR in Regulating the Serum Half-Life of Therapeutic Proteins Containing the Fc Domain of Human IgG1: A Comparative Study of the Affinity of Monoclonal Antibodies and Fc-Fusion Proteins to Human Neonatal FcR", J Immunol, 184 (4), DOI: https://doi.org/10.4049/jimmunol.0903296, Feb. 15, 2010, 1968-1976.
Tan, J. C. et al., "Characterization of interleukin-10 receptors on human and mouse cells", J. Biological Chemistry, 268(28), Oct. 5, 1993, 21053-21059.
Tisoncik, J. R. et al., "Into the eye of the cytokine storm", Microbiology and Molecular Biology Reviews, 76(1), doi:10.1128/MMBR.05015-11, Mar. 2012, 16-32.
Tu, Z. B. et al., "CCR9 in cancer: oncogenic role and therapeutic targeting", J. Hematology & Oncology, 9(10), doi: 10.1186/s13045-016-0236-7, Feb. 16, 2016, 1-9.
Xu, X. J. et al., "Cytokine release syndrome in cancer immunotherapy with chimeric antigen receptor engineered T cells", Cancer Letters, 343(2), http://dx.doi.org/10.1016/j.canlet.2013.10.004, Feb. 28, 2014, 172-178.
Xu, Z. et al., "Pathological findings of COVID-19 associated with acute respiratory distress syndrome", Lancet Respir Med., 8(4), doi: 10.1016/S2213-2600(20)30076-X, Feb. 17, 2020.
Zhang, S., et al., "QTY Code Enables Design of Detergent-Free Chemokine Receptors that Retain Ligand-Binding Activities," PNAS, vol. 115(37); pp. E8652-E8659, Aug. 2018.

* cited by examiner

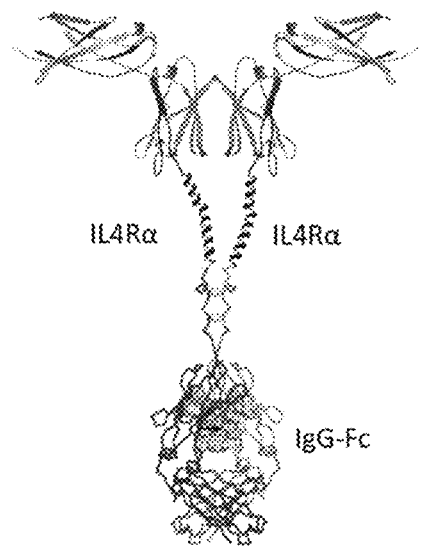
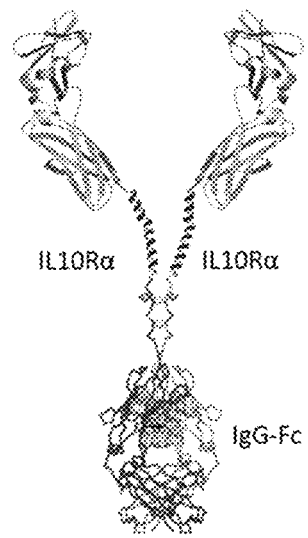
FIG. 2A
FIG. 2B
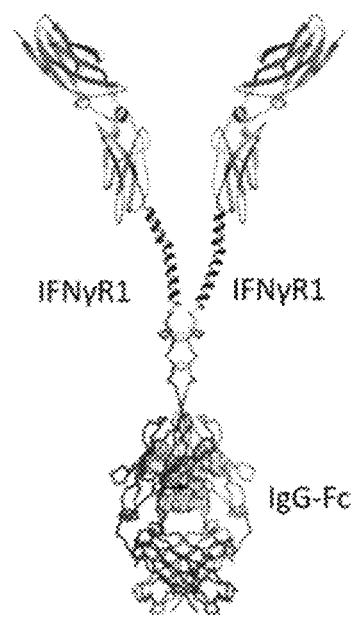
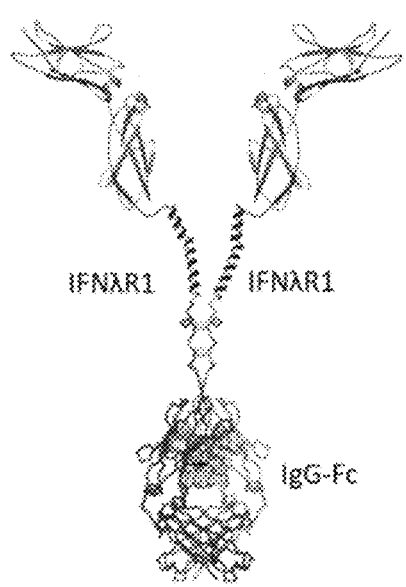
FIG. 2C
FIG. 2D

SEQUENCE LISTING

```
<160> NUMBER OF SEQ ID NOS: 16

<210> SEQ ID NO 1
<211> LENGTH: 20
<212> TYPE: PRT
<213> ORGANISM: Artificial Sequence
<220> FEATURE:
<223> OTHER INFORMATION: Synthetic

<400> SEQUENCE: 1

Gln Trp Thr Pro Thr Thr Ala Ala Gln Gln Gln Tyr Gln Thr Gln Ser
1               5                   10                  15

Gln Thr Tyr Thr
            20

<210> SEQ ID NO 2
<211> LENGTH: 24
<212> TYPE: PRT
<213> ORGANISM: Artificial Sequence
<220> FEATURE:
<223> OTHER INFORMATION: Synthetic

<400> SEQUENCE: 2

Thr Thr Gln Thr Ser Thr Gly Thr Tyr Ser Gln Gln Ser Thr Gln Ala
1               5                   10                  15

Gly Ala Cys Tyr Tyr Gln Thr Gln
            20

<210> SEQ ID NO 3
<211> LENGTH: 21
<212> TYPE: PRT
<213> ORGANISM: Artificial Sequence
<220> FEATURE:
<223> OTHER INFORMATION: Synthetic

<400> SEQUENCE: 3

Tyr Gln Thr Gln Pro Ser Gln Gln Thr Gln Gln Gln Thr Thr Ala Ala
1               5                   10                  15

Gly Gly Thr Thr Trp
            20

<210> SEQ ID NO 4
<211> LENGTH: 23
<212> TYPE: PRT
<213> ORGANISM: Artificial Sequence
<220> FEATURE:
<223> OTHER INFORMATION: Synthetic

<400> SEQUENCE: 4

Gln Gln Gln Gly Thr Ser Thr Ser Cys Thr Thr Thr Gln Ala Thr Cys
1               5                   10                  15

Gln Gln Cys Tyr Thr Ser Thr
            20
```

<210> SEQ ID NO 5
<211> LENGTH: 20
<212> TYPE: PRT
<213> ORGANISM: Artificial Sequence
<220> FEATURE:
<223> OTHER INFORMATION: Synthetic

<400> SEQUENCE: 5

Thr Thr Thr Tyr Tyr Ala Tyr Thr Gln Gln Gln Ser Gly Ala Gln Ala
1               5                   10                  15

Tyr Cys Gln Ala
            20

<210> SEQ ID NO 6
<211> LENGTH: 246
<212> TYPE: PRT
<213> ORGANISM: Homo sapiens

<400> SEQUENCE: 6

Met Ala Leu Leu Phe Leu Leu Pro Leu Val Met Gln Gly Val Ser Arg
1               5                   10                  15

Ala Glu Met Gly Thr Ala Asp Leu Gly Pro Ser Ser Val Pro Thr Pro
            20                  25                  30

Thr Asn Val Thr Ile Glu Ser Tyr Asn Met Asn Pro Ile Val Tyr Trp
        35                  40                  45

Glu Tyr Gln Ile Met Pro Gln Val Pro Val Phe Thr Val Glu Val Lys
    50                  55                  60

Asn Tyr Gly Val Lys Asn Ser Glu Trp Ile Asp Ala Cys Ile Asn Ile
65                  70                  75                  80

Ser His His Tyr Cys Asn Ile Ser Asp His Val Gly Asp Pro Ser Asn
                85                  90                  95

Ser Leu Trp Val Arg Val Lys Ala Arg Val Gly Gln Lys Glu Ser Ala
            100                 105                 110

Tyr Ala Lys Ser Glu Glu Phe Ala Val Cys Arg Asp Gly Lys Ile Gly
        115                 120                 125

Pro Pro Lys Leu Asp Ile Arg Lys Glu Glu Lys Gln Ile Met Ile Asp
    130                 135                 140

Ile Phe His Pro Ser Val Phe Val Asn Gly Asp Glu Gln Glu Val Asp
145                 150                 155                 160

Tyr Asp Pro Glu Thr Thr Cys Tyr Ile Arg Val Tyr Asn Val Tyr Val
                165                 170                 175

Arg Met Asn Gly Ser Glu Ile Gln Tyr Lys Ile Leu Thr Gln Lys Glu
            180                 185                 190

Asp Asp Cys Asp Glu Ile Gln Cys Gln Leu Ala Ile Pro Val Ser Ser
        195                 200                 205

Leu Asn Ser Gln Tyr Cys Val Ser Ala Glu Gly Val Leu His Val Trp
    210                 215                 220

Gly Val Thr Thr Glu Lys Ser Lys Glu Val Cys Ile Thr Ile Phe Asn
225                 230                 235                 240

Ser Ser Ile Lys Gly Ser
                245

<210> SEQ ID NO 7
<211> LENGTH: 247
<212> TYPE: PRT
<213> ORGANISM: Homo sapiens

```
<400> SEQUENCE: 7

Met Arg Pro Thr Leu Leu Trp Ser Leu Leu Leu Leu Gly Val Phe
1               5                   10                  15

Ala Ala Ala Ala Ala Pro Pro Asp Pro Leu Ser Gln Leu Pro Ala
                20                  25                  30

Pro Gln His Pro Lys Ile Arg Leu Tyr Asn Ala Glu Gln Val Leu Ser
        35                  40                  45

Trp Glu Pro Val Ala Leu Ser Asn Ser Thr Arg Pro Val Val Tyr Gln
    50                  55                  60

Val Gln Phe Lys Tyr Thr Asp Ser Lys Trp Phe Thr Ala Asp Ile Met
65                  70                  75                  80

Ser Ile Gly Val Asn Cys Thr Gln Ile Thr Ala Thr Glu Cys Asp Phe
                85                  90                  95

Thr Ala Ala Ser Pro Ser Ala Gly Phe Pro Met Asp Phe Asn Val Thr
                100                 105                 110

Leu Arg Leu Arg Ala Glu Leu Gly Ala Leu His Ser Ala Trp Val Thr
                115                 120                 125

Met Pro Trp Phe Gln His Tyr Arg Asn Val Thr Val Gly Pro Pro Glu
    130                 135                 140

Asn Ile Glu Val Thr Pro Gly Glu Gly Ser Leu Ile Ile Arg Phe Ser
145                 150                 155                 160

Ser Pro Phe Asp Ile Ala Asp Thr Ser Thr Ala Phe Phe Cys Tyr Tyr
                165                 170                 175

Val His Tyr Trp Glu Lys Gly Gly Ile Gln Gln Val Lys Gly Pro Phe
                180                 185                 190

Arg Ser Asn Ser Ile Ser Leu Asp Asn Leu Lys Pro Ser Arg Val Tyr
                195                 200                 205

Cys Leu Gln Val Gln Ala Gln Leu Leu Trp Asn Lys Ser Asn Ile Phe
    210                 215                 220

Arg Val Gly His Leu Ser Asn Ile Ser Cys Tyr Glu Thr Met Ala Asp
225                 230                 235                 240

Ala Ser Thr Glu Leu Gln Gln
                245

<210> SEQ ID NO 8
<211> LENGTH: 228
<212> TYPE: PRT
<213> ORGANISM: Homo sapiens

<400> SEQUENCE: 8

Met Ala Gly Pro Glu Arg Trp Gly Pro Leu Leu Leu Cys Leu Leu Gln
1               5                   10                  15

Ala Ala Pro Gly Arg Pro Arg Leu Ala Pro Pro Gln Asn Val Thr Leu
                20                  25                  30

Leu Ser Gln Asn Phe Ser Val Tyr Leu Thr Trp Leu Pro Gly Leu Gly
        35                  40                  45

Asn Pro Gln Asp Val Thr Tyr Phe Val Ala Tyr Gln Ser Ser Pro Thr
    50                  55                  60

Arg Arg Arg Trp Arg Glu Val Glu Glu Cys Ala Gly Thr Lys Glu Leu
65                  70                  75                  80

Leu Cys Ser Met Met Cys Leu Lys Lys Gln Asp Leu Tyr Asn Lys Phe
                85                  90                  95

Lys Gly Arg Val Arg Thr Val Ser Pro Ser Ser Lys Ser Pro Trp Val
                100                 105                 110
```

Glu Ser Glu Tyr Leu Asp Tyr Leu Phe Glu Val Pro Ala Pro Pro
            115                 120                 125

Val Leu Val Leu Thr Gln Thr Glu Glu Ile Leu Ser Ala Asn Ala Thr
130                 135                 140

Tyr Gln Leu Pro Pro Cys Met Pro Pro Leu Asp Leu Lys Tyr Glu Val
145                 150                 155                 160

Ala Phe Trp Lys Glu Gly Ala Gly Asn Lys Thr Leu Phe Pro Val Thr
                165                 170                 175

Pro His Gly Gln Pro Val Gln Ile Thr Leu Gln Pro Ala Ala Ser Glu
            180                 185                 190

His His Cys Leu Ser Ala Arg Thr Ile Tyr Thr Phe Ser Val Pro Lys
        195                 200                 205

Tyr Ser Lys Phe Ser Lys Pro Thr Cys Phe Leu Leu Glu Val Pro Glu
    210                 215                 220

Ala Asn Trp Ala
225

<210> SEQ ID NO 9
<211> LENGTH: 232
<212> TYPE: PRT
<213> ORGANISM: Homo sapiens

<400> SEQUENCE: 9

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Cys Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln His
225                 230

```
<210> SEQ ID NO 10
<211> LENGTH: 235
<212> TYPE: PRT
<213> ORGANISM: Homo sapiens

<400> SEQUENCE: 10

Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Tyr Phe Thr Val Thr Asn
225                 230                 235

<210> SEQ ID NO 11
<211> LENGTH: 529
<212> TYPE: PRT
<213> ORGANISM: Artificial Sequence
<220> FEATURE:
<223> OTHER INFORMATION: Synthetic

<400> SEQUENCE: 11

Met Ala Leu Leu Phe Leu Leu Pro Leu Val Met Gln Gly Val Ser Arg
1               5                   10                  15

Ala Glu Met Gly Thr Ala Asp Leu Gly Pro Ser Ser Val Pro Thr Pro
            20                  25                  30

Thr Asn Val Thr Ile Glu Ser Tyr Asn Met Asn Pro Ile Val Tyr Trp
        35                  40                  45

Glu Tyr Gln Ile Met Pro Gln Val Pro Val Phe Thr Val Glu Val Lys
    50                  55                  60

Asn Tyr Gly Val Lys Asn Ser Glu Trp Ile Asp Ala Cys Ile Asn Ile
65                  70                  75                  80

Ser His His Tyr Cys Asn Ile Ser Asp His Val Gly Asp Pro Ser Asn
                85                  90                  95
```

```
Ser Leu Trp Val Arg Val Lys Ala Arg Val Gly Gln Lys Glu Ser Ala
            100                 105                 110

Tyr Ala Lys Ser Glu Glu Phe Ala Val Cys Arg Asp Gly Lys Ile Gly
        115                 120                 125

Pro Pro Lys Leu Asp Ile Arg Lys Glu Glu Lys Gln Ile Met Ile Asp
130                 135                 140

Ile Phe His Pro Ser Val Phe Val Asn Gly Asp Glu Gln Glu Val Asp
145                 150                 155                 160

Tyr Asp Pro Glu Thr Thr Cys Tyr Ile Arg Val Tyr Asn Val Tyr Val
                165                 170                 175

Arg Met Asn Gly Ser Glu Ile Gln Tyr Lys Ile Leu Thr Gln Lys Glu
            180                 185                 190

Asp Asp Cys Asp Glu Ile Gln Cys Gln Leu Ala Ile Pro Val Ser Ser
        195                 200                 205

Leu Asn Ser Gln Tyr Cys Val Ser Ala Glu Gly Val Leu His Val Trp
210                 215                 220

Gly Val Thr Thr Glu Lys Ser Lys Glu Val Cys Ile Thr Ile Phe Asn
225                 230                 235                 240

Ser Ser Ile Lys Gly Ser Gln Trp Thr Pro Thr Thr Ala Ala Gln Gln
                245                 250                 255

Gln Tyr Gln Thr Gln Ser Gln Thr Tyr Thr Cys Phe Tyr Ile Lys Lys
            260                 265                 270

Thr Glu Thr Ser Gln Val Ala Pro Ala His His His His His His His
        275                 280                 285

His His His Gly Ser Lys Leu Val Asp Pro Arg Gly Pro Thr Ile Lys
        290                 295                 300

Pro Cys Pro Pro Cys Lys Cys Pro Ala Pro Asn Leu Leu Gly Gly Pro
305                 310                 315                 320

Ser Val Phe Ile Phe Pro Pro Lys Ile Lys Asp Val Leu Met Ile Ser
                325                 330                 335

Leu Ser Pro Ile Val Thr Cys Val Val Val Asp Val Ser Glu Asp Asp
            340                 345                 350

Pro Asp Val Gln Ile Ser Trp Phe Val Asn Asn Val Glu Val His Thr
        355                 360                 365

Ala Gln Thr Gln Thr His Arg Glu Asp Tyr Asn Ser Thr Leu Arg Val
370                 375                 380

Val Ser Ala Leu Pro Ile Gln His Gln Asp Trp Met Ser Gly Lys Glu
385                 390                 395                 400

Phe Lys Cys Lys Val Asn Asn Lys Asp Leu Pro Ala Pro Ile Glu Arg
                405                 410                 415

Thr Ile Ser Lys Pro Lys Gly Ser Val Arg Ala Pro Gln Val Tyr Val
            420                 425                 430

Leu Pro Pro Pro Glu Glu Glu Met Thr Lys Lys Gln Val Thr Leu Thr
        435                 440                 445

Cys Met Val Thr Asp Phe Met Pro Glu Asp Ile Tyr Val Glu Trp Thr
450                 455                 460

Asn Asn Gly Lys Thr Glu Leu Asn Tyr Lys Asn Thr Glu Pro Val Leu
465                 470                 475                 480

Asp Ser Asp Gly Ser Tyr Phe Met Tyr Ser Lys Leu Arg Val Glu Lys
                485                 490                 495

Lys Asn Trp Val Glu Arg Asn Ser Tyr Ser Cys Ser Val Val His Glu
            500                 505                 510
```

```
Gly Leu His Asn His His Thr Thr Lys Ser Phe Ser Arg Thr Pro Gly
            515                 520                 525

Lys

<210> SEQ ID NO 12
<211> LENGTH: 532
<212> TYPE: PRT
<213> ORGANISM: Artificial Sequence
<220> FEATURE:
<223> OTHER INFORMATION: Synthetic

<400> SEQUENCE: 12

Met Arg Pro Thr Leu Leu Trp Ser Leu Leu Leu Leu Gly Val Phe
 1               5                  10                  15

Ala Ala Ala Ala Ala Pro Pro Asp Pro Leu Ser Gln Leu Pro Ala
                20                  25                  30

Pro Gln His Pro Lys Ile Arg Leu Tyr Asn Ala Glu Gln Val Leu Ser
                35                  40                  45

Trp Glu Pro Val Ala Leu Ser Asn Ser Thr Arg Pro Val Val Tyr Gln
            50                  55                  60

Val Gln Phe Lys Tyr Thr Asp Ser Lys Trp Phe Thr Ala Asp Ile Met
 65                 70                  75                  80

Ser Ile Gly Val Asn Cys Thr Gln Ile Thr Ala Thr Glu Cys Asp Phe
                85                  90                  95

Thr Ala Ala Ser Pro Ser Ala Gly Phe Pro Met Asp Phe Asn Val Thr
                100                 105                 110

Leu Arg Leu Arg Ala Glu Leu Gly Ala Leu His Ser Ala Trp Val Thr
            115                 120                 125

Met Pro Trp Phe Gln His Tyr Arg Asn Val Thr Val Gly Pro Pro Glu
            130                 135                 140

Asn Ile Glu Val Thr Pro Gly Glu Gly Ser Leu Ile Ile Arg Phe Ser
145                 150                 155                 160

Ser Pro Phe Asp Ile Ala Asp Thr Ser Thr Ala Phe Phe Cys Tyr Tyr
                165                 170                 175

Val His Tyr Trp Glu Lys Gly Gly Ile Gln Gln Val Lys Gly Pro Phe
            180                 185                 190

Arg Ser Asn Ser Ile Ser Leu Asp Asn Leu Lys Pro Ser Arg Val Tyr
            195                 200                 205

Cys Leu Gln Val Gln Ala Gln Leu Leu Trp Asn Lys Ser Asn Ile Phe
            210                 215                 220

Arg Val Gly His Leu Ser Asn Ile Ser Cys Tyr Glu Thr Met Ala Asp
225                 230                 235                 240

Ala Ser Thr Glu Leu Gln Gln Thr Thr Gln Thr Ser Thr Gly Thr Tyr
                245                 250                 255

Ser Gln Gln Ser Thr Gln Ala Gly Ala Cys Tyr Tyr Gln Thr Gln Lys
            260                 265                 270

Tyr Arg Gly Thr Glu Thr Ser Gln Val Ala Pro Ala His His His
            275                 280                 285

His His His His His Gly Ser Lys Leu Val Asp Pro Arg Gly Pro
        290                 295                 300

Thr Ile Lys Pro Cys Pro Pro Cys Lys Cys Pro Ala Pro Asn Leu Leu
305                 310                 315                 320

Gly Gly Pro Ser Val Phe Ile Phe Pro Pro Lys Ile Lys Asp Val Leu
                325                 330                 335
```

-continued

```
Met Ile Ser Leu Ser Pro Ile Val Thr Cys Val Val Asp Val Ser
            340                 345                 350

Glu Asp Asp Pro Asp Val Gln Ile Ser Trp Phe Val Asn Asn Val Glu
        355                 360                 365

Val His Thr Ala Gln Thr Gln Thr His Arg Glu Asp Tyr Asn Ser Thr
    370                 375                 380

Leu Arg Val Val Ser Ala Leu Pro Ile Gln His Gln Asp Trp Met Ser
385                 390                 395                 400

Gly Lys Glu Phe Lys Cys Lys Val Asn Asn Lys Asp Leu Pro Ala Pro
                405                 410                 415

Ile Glu Arg Thr Ile Ser Lys Pro Lys Gly Ser Val Arg Ala Pro Gln
            420                 425                 430

Val Tyr Val Leu Pro Pro Glu Glu Glu Met Thr Lys Lys Gln Val
        435                 440                 445

Thr Leu Thr Cys Met Val Thr Asp Phe Met Pro Glu Asp Ile Tyr Val
    450                 455                 460

Glu Trp Thr Asn Asn Gly Lys Thr Glu Leu Asn Tyr Lys Asn Thr Glu
465                 470                 475                 480

Pro Val Leu Asp Ser Asp Gly Ser Tyr Phe Met Tyr Ser Lys Leu Arg
                485                 490                 495

Val Glu Lys Lys Asn Trp Val Glu Arg Asn Ser Tyr Ser Cys Ser Val
            500                 505                 510

Val His Glu Gly Leu His Asn His His Thr Thr Lys Ser Phe Ser Arg
        515                 520                 525

Thr Pro Gly Lys
    530

<210> SEQ ID NO 13
<211> LENGTH: 512
<212> TYPE: PRT
<213> ORGANISM: Artificial Sequence
<220> FEATURE:
<223> OTHER INFORMATION: Synthetic

<400> SEQUENCE: 13

Met Ala Gly Pro Glu Arg Trp Gly Pro Leu Leu Leu Cys Leu Leu Gln
1               5                   10                  15

Ala Ala Pro Gly Arg Pro Arg Leu Ala Pro Pro Gln Asn Val Thr Leu
            20                  25                  30

Leu Ser Gln Asn Phe Ser Val Tyr Leu Thr Trp Leu Pro Gly Leu Gly
        35                  40                  45

Asn Pro Gln Asp Val Thr Tyr Phe Val Ala Tyr Gln Ser Ser Pro Thr
    50                  55                  60

Arg Arg Arg Trp Arg Glu Val Glu Glu Cys Ala Gly Thr Lys Glu Leu
65                  70                  75                  80

Leu Cys Ser Met Met Cys Leu Lys Lys Gln Asp Leu Tyr Asn Lys Phe
                85                  90                  95

Lys Gly Arg Val Arg Thr Val Ser Pro Ser Ser Lys Ser Pro Trp Val
            100                 105                 110

Glu Ser Glu Tyr Leu Asp Tyr Leu Phe Glu Val Glu Pro Ala Pro Pro
        115                 120                 125

Val Leu Val Leu Thr Gln Thr Glu Glu Ile Leu Ser Ala Asn Ala Thr
    130                 135                 140

Tyr Gln Leu Pro Pro Cys Met Pro Pro Leu Asp Leu Lys Tyr Glu Val
145                 150                 155                 160
```

```
Ala Phe Trp Lys Glu Gly Ala Gly Asn Lys Thr Leu Phe Pro Val Thr
                165                 170                 175

Pro His Gly Gln Pro Val Gln Ile Thr Leu Gln Pro Ala Ala Ser Glu
            180                 185                 190

His His Cys Leu Ser Ala Arg Thr Ile Tyr Thr Phe Ser Val Pro Lys
        195                 200                 205

Tyr Ser Lys Phe Ser Lys Pro Thr Cys Phe Leu Leu Glu Val Pro Glu
    210                 215                 220

Ala Asn Trp Ala Tyr Gln Thr Gln Pro Ser Gln Gln Thr Gln Gln Gln
225                 230                 235                 240

Thr Thr Ala Ala Gly Gly Thr Thr Trp Lys Thr Leu Met Gly Asn Thr
                245                 250                 255

Glu Thr Ser Gln Val Ala Pro Ala His His His His His His His His
            260                 265                 270

His His Gly Ser Lys Leu Val Asp Pro Arg Gly Pro Thr Ile Lys Pro
        275                 280                 285

Cys Pro Pro Cys Lys Cys Pro Ala Pro Asn Leu Leu Gly Gly Pro Ser
290                 295                 300

Val Phe Ile Phe Pro Pro Lys Ile Lys Asp Val Leu Met Ile Ser Leu
305                 310                 315                 320

Ser Pro Ile Val Thr Cys Val Val Val Asp Val Ser Glu Asp Asp Pro
                325                 330                 335

Asp Val Gln Ile Ser Trp Phe Val Asn Asn Val Glu Val His Thr Ala
            340                 345                 350

Gln Thr Gln Thr His Arg Glu Asp Tyr Asn Ser Thr Leu Arg Val Val
        355                 360                 365

Ser Ala Leu Pro Ile Gln His Gln Asp Trp Met Ser Gly Lys Glu Phe
    370                 375                 380

Lys Cys Lys Val Asn Asn Lys Asp Leu Pro Ala Pro Ile Glu Arg Thr
385                 390                 395                 400

Ile Ser Lys Pro Lys Gly Ser Val Arg Ala Pro Gln Val Tyr Val Leu
                405                 410                 415

Pro Pro Pro Glu Glu Glu Met Thr Lys Lys Gln Val Thr Leu Thr Cys
            420                 425                 430

Met Val Thr Asp Phe Met Pro Glu Asp Ile Tyr Val Glu Trp Thr Asn
        435                 440                 445

Asn Gly Lys Thr Glu Leu Asn Tyr Lys Asn Thr Glu Pro Val Leu Asp
    450                 455                 460

Ser Asp Gly Ser Tyr Phe Met Tyr Ser Lys Leu Arg Val Glu Lys Lys
465                 470                 475                 480

Asn Trp Val Glu Arg Asn Ser Tyr Ser Cys Ser Val Val His Glu Gly
                485                 490                 495

Leu His Asn His His Thr Thr Lys Ser Phe Ser Arg Thr Pro Gly Lys
            500                 505                 510

<210> SEQ ID NO 14
<211> LENGTH: 518
<212> TYPE: PRT
<213> ORGANISM: Artificial Sequence
<220> FEATURE:
<223> OTHER INFORMATION: Synthetic
```

<400> SEQUENCE: 14

```
Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
            85                  90                  95

Asp Asn Tyr Thr Leu Asp Leu Trp Ala Gly Gln Gln Leu Leu Trp Lys
        100                 105                 110

Gly Ser Phe Lys Pro Ser Glu His Val Lys Pro Arg Ala Pro Gly Asn
    115                 120                 125

Leu Thr Val His Thr Asn Val Ser Asp Thr Leu Leu Leu Thr Trp Ser
130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
            165                 170                 175

Val Thr Tyr Leu Glu Pro Ser Leu Arg Ile Ala Ala Ser Thr Leu Lys
        180                 185                 190

Ser Gly Ile Ser Tyr Arg Ala Arg Val Arg Ala Trp Ala Gln Cys Tyr
    195                 200                 205

Asn Thr Thr Trp Ser Glu Trp Ser Pro Ser Thr Lys Trp His Asn Ser
210                 215                 220

Tyr Arg Glu Pro Phe Glu Gln His Gln Gln Gly Thr Ser Thr Ser
225                 230                 235                 240

Cys Thr Thr Thr Gln Ala Thr Cys Gln Gln Cys Tyr Thr Ser Thr Thr
            245                 250                 255

Lys Ile Lys Lys Glu Thr Glu Thr Ser Gln Val Ala Pro Ala His His
        260                 265                 270

His His His His His Gly Ser Lys Leu Val Asp Pro Arg
    275                 280                 285

Gly Pro Thr Ile Lys Pro Cys Pro Pro Cys Lys Cys Pro Ala Pro Asn
290                 295                 300

Leu Leu Gly Gly Pro Ser Val Phe Ile Phe Pro Pro Lys Ile Lys Asp
305                 310                 315                 320

Val Leu Met Ile Ser Leu Ser Pro Ile Val Thr Cys Val Val Val Asp
            325                 330                 335

Val Ser Glu Asp Asp Pro Asp Val Gln Ile Ser Trp Phe Val Asn Asn
        340                 345                 350

Val Glu Val His Thr Ala Gln Thr Gln Thr His Arg Glu Asp Tyr Asn
    355                 360                 365

Ser Thr Leu Arg Val Val Ser Ala Leu Pro Ile Gln His Gln Asp Trp
370                 375                 380

Met Ser Gly Lys Glu Phe Lys Cys Lys Val Asn Asn Lys Asp Leu Pro
385                 390                 395                 400

Ala Pro Ile Glu Arg Thr Ile Ser Lys Pro Lys Gly Ser Val Arg Ala
            405                 410                 415
```

-continued

Pro Gln Val Tyr Val Leu Pro Pro Glu Glu Met Thr Lys Lys
        420                 425                 430

Gln Val Thr Leu Thr Cys Met Val Thr Asp Phe Met Pro Glu Asp Ile
    435                 440                 445

Tyr Val Glu Trp Thr Asn Asn Gly Lys Thr Glu Leu Asn Tyr Lys Asn
450                 455                 460

Thr Glu Pro Val Leu Asp Ser Asp Gly Ser Tyr Phe Met Tyr Ser Lys
465                 470                 475                 480

Leu Arg Val Glu Lys Lys Asn Trp Val Glu Arg Asn Ser Tyr Ser Cys
                485                 490                 495

Ser Val Val His Glu Gly Leu His Asn His His Thr Thr Lys Ser Phe
            500                 505                 510

Ser Arg Thr Pro Gly Lys
        515

<210> SEQ ID NO 15
<211> LENGTH: 522
<212> TYPE: PRT
<213> ORGANISM: Artificial Sequence
<220> FEATURE:
<223> OTHER INFORMATION: Synthetic

<400> SEQUENCE: 15

Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Tyr Phe Thr Val Thr Asn Thr Thr Tyr Tyr
225                 230                 235                 240

Ala Tyr Thr Gln Gln Gln Ser Gly Ala Gln Ala Tyr Cys Gln Ala Gln
                245                 250                 255

```
Gln Leu Tyr Val Arg Arg Arg Lys Lys Thr Glu Thr Ser Gln Val Ala
            260                 265                 270

Pro Ala His His His His His His His His Gly Ser Lys Leu
        275                 280                 285

Val Asp Pro Arg Gly Pro Thr Ile Lys Pro Cys Pro Cys Lys Cys
    290                 295                 300

Pro Ala Pro Asn Leu Leu Gly Gly Pro Ser Val Phe Ile Phe Pro Pro
305                 310                 315                 320

Lys Ile Lys Asp Val Leu Met Ile Ser Leu Ser Pro Ile Val Thr Cys
                325                 330                 335

Val Val Val Asp Val Ser Glu Asp Asp Pro Val Gln Ile Ser Trp
                340                 345                 350

Phe Val Asn Asn Val Glu Val His Thr Ala Gln Thr Gln Thr His Arg
                355                 360                 365

Glu Asp Tyr Asn Ser Thr Leu Arg Val Val Ser Ala Leu Pro Ile Gln
            370                 375                 380

His Gln Asp Trp Met Ser Gly Lys Glu Phe Lys Cys Lys Val Asn Asn
385                 390                 395                 400

Lys Asp Leu Pro Ala Pro Ile Glu Arg Thr Ile Ser Lys Pro Lys Gly
                405                 410                 415

Ser Val Arg Ala Pro Gln Val Tyr Val Leu Pro Pro Pro Glu Glu Glu
                420                 425                 430

Met Thr Lys Lys Gln Val Thr Leu Thr Cys Met Val Thr Asp Phe Met
                435                 440                 445

Pro Glu Asp Ile Tyr Val Glu Trp Thr Asn Asn Gly Lys Thr Glu Leu
    450                 455                 460

Asn Tyr Lys Asn Thr Glu Pro Val Leu Asp Ser Asp Gly Ser Tyr Phe
465                 470                 475                 480

Met Tyr Ser Lys Leu Arg Val Glu Lys Lys Asn Trp Val Glu Arg Asn
                485                 490                 495

Ser Tyr Ser Cys Ser Val Val His Glu Gly Leu His Asn His His Thr
                500                 505                 510

Thr Lys Ser Phe Ser Arg Thr Pro Gly Lys
            515                 520

<210> SEQ ID NO 16
<211> LENGTH: 23
<212> TYPE: PRT
<213> ORGANISM: Artificial Sequence
<220> FEATURE:
<223> OTHER INFORMATION: Synthetic

<400> SEQUENCE: 16

Pro Arg Gly Pro Thr Ile Lys Pro Cys Pro Cys Lys Cys Pro Ala
1               5                  10                  15

Pro Asn Leu Leu Gly Gly Pro
            20
```

QTY FC FUSION WATER SOLUBLE RECEPTOR PROTEINS

RELATED APPLICATION

This application claims the benefit of U.S. Provisional Application No. 62/994,433 filed Mar. 25, 2020. The entire teachings of the above-referenced application are incorporated herein by reference.

BACKGROUND OF THE INVENTION

Chimeric antigen receptor (CAR) T-cell therapy is a cellular immunotherapy in which patient's T cells are engineered in vitro to target and eliminate cancer cells in vivo. In CAR-T treatment, the T cells from a patient's blood are extracted by apheresis. The gene for a specific receptor (CAR) which binds to a certain tumor target is delivered to the T cells by viral vector or non-viral transposon methods (Ittershagen et al., 2019; Jain & Davila, 2018; Srivastava & Riddell, 2015). At present, two anti-CD19 CAR-T products have been approved by the US FDA for the treatment of B-cell acute lymphoblastic leukemia and non-Hodgkin lymphoma; CAR-T therapy for other cancer types are undergoing vigorous clinical studies. CAR-T therapy holds great promise for treating hematologic malignancies, and recent clinical evidence has indicated that similar approaches can also be used to treat solid tumors (Baybutt et al., 2019).

However, there are several side effects during CAR-T treatment that is potentially fatal to the patients, including: cytokine release syndrome (CRS), neurologic events, neutropenia and anemia (Xu & Tang, 2014). Among all the side effects, CRS is considered as a significant one that can be life-threatening. Cytokines are immune mediators essential in many bodily actions in human. Yet, a large and rapid release of cytokines into the blood from immune cells can induce "cytokine storm" ("CRS"). Most patients with CRS develop a mild flu-like reaction such as fever, fatigue, headache and rash. However, the reaction may progress to an uncontrolled, systemic inflammatory response with extreme pyrexia and become life-threatening (Shimabukuro-Vornhagen et al., 2018).

Manifestation of CRS can also be triggered by viral infections such as influenza and hepatitis virus (de Jong et al., 2006; Savarin & Bergmann, 2018; Tisoncik et al., 2012). The current COVID-19 (Coronavirus Disease 2019) global pandemic involves CRS in many stages of its pathological course that causes lung fibrosis, acute respiratory distress syndrome, and eventually leads to multiple organ failure (Huang et al., 2020; Xu et al., 2020). Other conditions, including graft-versus-host disease, sepsis, Ebola, avian influenza, smallpox, and systemic inflammatory response syndrome, also involve extensive release of undesired cytokines (Drazen, 2000). To alleviate the symptoms and treat the disease, it is important to remove the excessive cytokines efficiently and rapidly.

Fc fusion proteins, an immunoglobulin Fc region directly linked to, for example, an extracellular domain of a receptor, are therapeutic agents that can bind and eliminate ligands. An example of a fusion protein is etanercept, an anti-TNF drug currently marketed as a treatment for a variety of inflammatory diseases. Although the therapeutic protein has been found to be safe and effective, the utilization of the molecule is limited by an unexpected short serum half life (80-120 hours about 4 days) when administered by subcutaneous injection. Other attempts to develop Fc fusion proteins to clear aberrant protein expression has been limited. However, improved strategies for Fc fusion protein design is needed.

SUMMARY OF THE INVENTION

The application provides novel Fc fusion receptor proteins with a novel linking region comprising a QTY membrane region.

The applicants have previously devised a novel tool called "QTY code" which regulates the water solubility of redesigned membrane proteins through pairwise substituting hydrophobic amino acids with hydrophilic ones (U.S. Pat. No. 8,637,452 and WO2015/148820 (Zhang et al.) and Zhang et al., 2018, QTY code enables design of detergent-free chemokine receptors that retain ligand-binding activities. Proc Natl Acad Sci USA, 115(37), E8652-E8659). Hydrophobic amino acids Leu, Val, Ile and Phe are exchanged by hydrophilic Gln, Thr and Tyr in the transmembrane regions of a receptor, based on the structural and electron density maps similarity in their side chains. The QTY code has provided flexibility in studying the physiological and functional properties of GPCRs, as well as promoting their utilization, without the requirements of time consuming and expensive detergent screening or use of nanodisks.

The applicants reported the QTY code design of cytokine receptors comprising an Fc domain, QTY transmembrane regions and extracellular domains of cytokine receptors, including interleukin and interferon receptors. These QTY code designed receptors show ligand-binding properties similar to their counterpart native receptors without the presence of hydrophobic patches. The exemplified receptors were fused with Fc domain of mouse IgG2a protein to form an antibody-like structure. These Fc-fusion receptors were expressed and purified in an *E. coli* system with sufficient yield (~mg/L) in LB media. We also showed that the binding affinity of these QTY receptors approximated isolated native receptors on solution-based assays. These QTY code design of functional, water-soluble Fc-fusion cytokine receptors can be used clinically as decoy therapy to rapidly remove excessive cytokines in the setting of hyperactive immune reactions during CRS or "cytokine storm".

The invention includes QTY Fc Fusion proteins comprising an Fc domain or fragment thereof, a QTY modified transmembrane domain and one or more extracellular domains (ECD) of a cytokine receptor. For example, the Fc fusion proteins of the invention can have the formula:

N-terminus (ECD-QTY TM-Fc-Domain) C-terminus

Each domain or region can be directly or indirectly linked or fused to its adjacent domain. For example, additional peptide linkers (one or more glycine residues or restriction sites) can be used to link domains. Additional domains (such as an immunoglobulin hinge region, restriction sites, or tags) can also be used.

The invention also includes pharmaceutical compositions comprising QTY Fc fusion proteins, methods of manufacture QTY Fc fusion proteins and methods of using QTY Fc fusion proteins.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 2A-2D. Schematic illustration for Fc fused QTY variant cytokine receptors with antibody-like structure. (FIG. 2A) IL4Rα$^{QTY}$-Fc; (FIG. 2B) IL10Rα$^{QTY}$-Fc; (FIG. 2C) IFNγR1$^{QTY}$-Fc; (FIG. 2D) IFNλR1$^{QTY}$-Fc. These illustrations are not to scale and the receptors parts are significantly emphasized for clarity.

(FIG. 3A) IL4Rα$^{QTY}$-Fc with IL4; (FIG. 3B) IL10Rα$^{QTY}$-Fc with IL10; (FIG. 3C) IFNγR1$^{QTY}$-Fc with IFNγ; (FIG. 3D) IFNγR1$^{QTY}$-Fc with IL29.

DETAILED DESCRIPTION OF THE INVENTION

Figure 1A:
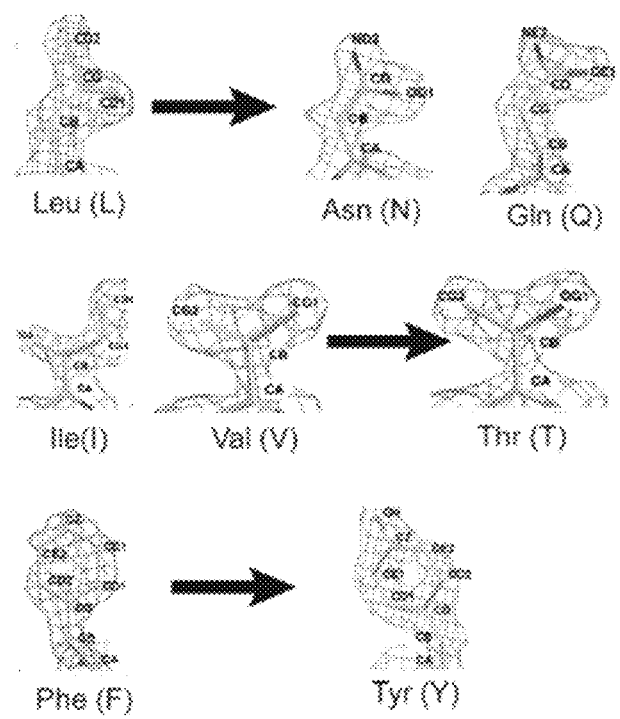
FIGS. 1A and 1B illustrate the QTY strategy wherein the amino acids Q, T and Y, together with other amino acids, can form alpha helical domains that mimic a transmembrane region. (A) Crystallographic electronic density maps of the following amino acids: Leucine (L), Asparagine (N), Glutamine (Q), Isoleucine (I), Valine (V), Threonine (T), Phenylalanine (F) and Tyrosine (Y). The density maps of L, N and Q are very similar. Likewise, the density maps of I, V and T are similar, and the density maps of F and Y are similar. (B) Helical wheels before and after applying the QTY code to transmembrane helical segment 1 (TM1) of CXCR4. Amino acids that interact with water molecules are light blue in color. The QTY code conversions render the alpha-helical segment water-soluble.

A description of preferred embodiments of the invention follows.

QTY Transmembrane Domain

The present invention is directed to a method of designing, selecting and/or producing QTY Fc fusion receptor proteins, these proteins produced by the process, compositions comprising said polypeptides, and methods of use thereof. In particular, the method relates to a process for designing proteins using the "QTY code Principle," changing the water-insoluble amino acids (Leu, Ile, Val and Phe, or the single letter code L, I, V, F) into water-soluble, non-ionic amino acids (Gln, Thr and Tyr, or the single letter code Q, T, Y). Furthermore, two additional non-ionic amino acids Asn (N) and Ser (S) may also be used for the substitution for L, I and V but not for F. In the embodiments discussed below, it is to be understood that Asn (N) and Ser (S) are envisioned as being substitutable for Q and T (as a variant is described) or L, I or V (as a native protein is described). For the purposes of brevity, however, the application does not explicitly state these alternative embodiments.

The invention utilizes a modified, synthetic, and/or non-naturally occurring, α-helical domain(s) and water-soluble polypeptides mimicking transmembrane regions (e.g., "sTMs" or "QTY TMs") comprising such modified α-helical domain(s), wherein the modified α-helical domain(s) comprise an amino acid sequence in which a plurality of hydrophobic amino acid residues (L, I V, F) within a α-helical domain of a native membrane protein are replaced with hydrophilic, non-ionic amino acid residues (Q, T, T, Y, respectively, or "Q, T, Y") and/or N and S. The invention also encompasses a method of preparing a water-soluble polypeptide comprising replacing a plurality of hydrophobic amino acid residues (L, I V, F) within the α-helical domain(s) of a native membrane protein with hydrophilic, non-ionic amino acid residues (Q, T, Y). The invention additionally encompasses a polypeptide prepared by replacing a plurality of hydrophobic amino acid residues (L, I V, F) within the α-helical domain of a native membrane protein with hydrophilic, non-ionic amino acid residues (Q, T, Y., respectively). The variant can be characterized by the name of the parent or native protein (e.g., the interferon receptor, IFNR) preceded or followed by the abbreviation "QTY" (e.g., QTY IFNR or IFNR-QTY).

The α-helical domain can be a transmembrane α-helical domains of a native cytokine receptor. For example, the receptor can bind one or more interferons or interleukins (e.g. IL-1, IL-2, IL-3, IL4, IL-5, IL6, IL8, IL10, IL12, IL-17, . . . or IL-22. In a further aspect, the native membrane protein is a mammalian protein. The proteins of the invention are preferably human. For the purposes of being concise, references to specific receptors (e.g., an interleukin or interferon receptor) are intended to refer to both mammalian, generally, and, in the alternative, human, specifically. The QTY transmembrane domain can be from the same or different protein as the extracellular domains. For the purposes of this invention, the word "native" is intended to refer to the protein (or α-helical domain) prior to water solubilization design in accordance with the methods described herein.

The hydrophilic residues (which replace one or more hydrophobic residues in the α-helical domain of a native membrane protein) are selected from the group consisting of glutamine (Q), threonine (T), tyrosine (Y) and any combination thereof. In additional aspects, the hydrophobic residues selected from leucine (L), isoleucine (I), valine (V) and phenylalanine (F) are replaced. Specifically, the phenylalanine residues of the α-helical domain of the protein are replaced with tyrosine; the isoleucine and/or valine residues of the α-helical domain of the protein are replaced with threonine; and/or the leucine residues of the α-helical domain of the protein are replaced with glutamine.

Preferred receptor proteins of the invention possess the ability to bind the ligand which normally binds to the wild type or native membrane protein. In preferred embodiments, the amino acids within potential ligand binding sites of the native membrane protein are not replaced and/or the sequences of the extracellular of the native membrane polypeptide are identical.

For example, the following table provides QTY TM domains that can be used.

| Parent Protein | QTY Sequence | SEQ ID NO |
|---|---|---|
| Human Interferon Gamma 1 | QWTPTTAAQQQYQT QSQTYT | SEQ ID NO. 1 |
| Human Interferon Gamma 2 | TTQTSTGTYSQQST QAGACYYQTQ | SEQ ID NO. 2 |
| Human Interferon1 Lambda | YQTQPSQQTQQQTT AAGGTTW | SEQ ID NO. 3 |
| Human Interleukin-4 receptor subunit alpha | QQQGTSTSCTTTQA TCQQCYTST | SEQ ID NO. 4 |
| Human IL-10 receptor subunit alpha | TTTYYAYTQQQSGA QAYCQA | SEQ ID NO. 5 |

The QTY TM Domain can be a complete transmembrane domain or a portion thereof. For example, the QTY TM Domain can be the first 1, 2, 3, 4, or more helical turns (approximately 4 amino acids per helical turn) from the extracellular surface of the transmembrane region. Additionally, amino acids that are proximal and/or external to the transmembrane region can be included. For example, the native amino acids of the parent protein that are 1, 2, 3, 4, or 5 amino acids upstream and/or downstream of the transmembrane region can be included in the QTY TM Domain. Optimizing the amino acids that couple or fuse the ligand binding domain to the QTY TM Domain can control the presentation of the ligand binding domain faces to the desired ligand. For example, where ligand binding domains (e.g., an alpha and beta subunit) are oriented to present an inward face (the surface of a first ligand binding domain that is proximal to the surface of a second ligand binding domain) which increases affinity or specificity for a ligand, amino acids coupling the ligand binding domain to the QTY TM domain can preserve the three-dimensional presentation of the ligand binding domain(s).

The QTY TM Domain can include one or more amino acid variants that present an additional reactive moiety for functionalization. For example, a hydroxyl, carboxyl or amino group on an amino acid side chain can be further functionalized, for example with a polyethylene glycol or carbohydrate. Further functionalization can improve serum half-life of the Fc fusion receptor protein.

Ligand Binding Domains

The QTY Fc fusion receptor protein also comprises one or more ligand-binding domains. A full antibody or immunoglobulin is typically characterized by two ligand binding domains (the variable antibody chains). Similarly, the invention contemplates Fc fusion proteins with one ligand binding domain (e.g., a single chain immunoglobulin or fragment thereof) or two or more ligand binding domains (e.g., a double chain immunoglobulin or fragment thereof). Where two or more ligand binding domains are presented, the ligand binding domains can be the same (e.g., homodimers) or different (heterodimers). Heterodimers can be desirable where the native receptor (parent protein) has an alpha and beta subunit. Fc fusion receptor proteins using two or more native subunits is referred to herein as natively heterodimeric. The invention also contemplates Fc fusion receptor proteins comprising two or more ligand binding domains that are not native. In this case, the Fc fusion receptor protein can comprise an alpha subunit ligand binding domain and a beta subunit ligand binding domain, each linked to the Fc domain with the same or different QTY TM domain.

For example, a ligand binding domain can comprise one or more extracellular domains of a membrane protein, such as a receptor molecule. For example, the extra-cellular domain of a membrane-anchored receptor or a ligand-binding fragment thereof can be used. The extracellular domain can preferably be derived from the same transmembrane protein as the transmembrane domain.

The receptor can be selected from death receptors, growth factor receptors and cytokine receptors. More preferably, the receptor is selected from interferon receptors, interleukin receptors, CD95 (APO-1; Fas), TRAIL receptors, TNF receptors, VEGF receptors, an interleukin receptor such as IL-15Rα. Most preferably the receptor is CD95, a TRAIL receptor, e.g., the TRAIL receptor-1, the TRAIL receptor-2, the TRAIL receptor-3 or the TRAIL receptor-4 or a TNF receptor, e.g., the TNF receptor-1 or the TNF receptor-2. Examples of interleukin receptors include IL-2R, IL-3R, IL-4R, IL-5R, IL-6R, IL-7R, IL-9R, IL-10R, IL-11R, IL-12R, IL-13R, IL-15R, IL-17R, IL-18R, IL-20R, IL-21R, IL-22R, IL-23R, IL-27R, IL-35R. Type II cytokine receptors suitable for use in the invention are multimeric receptors composed of heterologous subunits and are receptors mainly for interferons. This family of receptors includes, but is not limited to, receptors for interferon alpha, interferon beta and interferon gamma, IL10, IL22, and tissue factors.

Examples of Extracellular Domains include:

Human Interferon Gamma 1 ECD:
(SEQ ID NO. 6)
MALLFLLPLVMQGVSRAEMGTADLGPSSVPTPTNVTIESYNMNPIVYWEY

QIMPQVPVFTVEVKNYGVKNSEWIDACINISHHYCNISDHVGDPSNSLWV

RVKARVGQKESAYAKSEEFAVCRDGKIGPPKLDIRKEEKQIMIDIFHPSV

FVNGDEQEVDYDPETTCYIRVYNVYVRMNGSEIQYKILTQKEDDCDEIQC

QLAIPVSSLNSQYCVSAEGVLHVWGVTTEKSKEVCITIFNSSIKGS.

Human Interferon Gamma 2 ECD:
(SEQ ID NO. 7)
MRPTLLWSLLLLLGVFAAAAAAPPDPLSQLPAPQHPKIRLYNAEQVLSWE

PVALSNSTRPVVYQVQFKYTDSKWFTADIIVISIGVNCTQITATECDFTA

ASPSAGFPMDFNVTLRLRAELGALHSAWVTMPWFQHYRNVTVGPPENIEV

TPGEGSLIIRFSSPFDIADTSTAFFCYYVHYWEKGGIQQVKGPFRSNSIS

LDNLKPSRVYCLQVQAQLLWNKSNIFRVGHLSNISCYETMADASTELQQ.

Human Interferon Lambda 1 ECD:
(SEQ ID NO. 8)
MAGPERWGPLLLCLLQAAPGRPRLAPPQNVTLLSQNFSVYLTWLPGLGNP

QDVTYFVAYQSSPTRRRWREVEECAGTKELLCSMIVICLKKQDLYNKFKG

RVRTVSPSSKSPWVESEYLDYLFEVEPAPPVLVLTQTEEILSANATYQLP

PCMPPLDLKYEVAFWKEGAGNKTLFPVTPHGQPVQITLQPAASEHHCLSA

RTIYTFSVPKYSKFSKPTCFLLEVPEANWA.

Human Interleukin-4 receptor subunit
alpha ECD:
(SEQ ID NO. 9)
MGWLCSGLLFPVSCLVLLQVASSGNMKVLQEPTCVSDYMSISTCEWKMNG

PTNCSTELRLLYQLVFLLSEAHTCIPENNGGAGCVCHLLMDDVVSADNYT

LDLWAGQQLLWKGSFKPSEHVKPRAPGNLTVHTNVSDTLLLTWSNPYPPD

NYLYNHLTYAVNIWSENDPADFRIYNVTYLEPSLRIAASTLKSGISYRAR

VRAWAQCYNTTWSEWSPSTKWHNSYREPFEQH.

Human IL-10 receptor subunit alpha ECD:
(SEQ ID NO. 10)
MLPCLVVLLAALLSLRLGSDAHGTELPSPPSVWFEAEFFHHILHWTPIPN

QSESTCYEVALLRYGIESWNSISNCSQTLSYDLTAVTLDLYHSNGYRARV

RAVDGSRHSNWTVTNTRFSVDEVTLTVGSVNLEIHNGFILGKIQLPRPKM

APANDTYESIFSHFREYEIAIRKVPGNFTFTHKKVKHENFSLLTSGEVGE

FCVQVKPSVASRSNKGMWSKEECISLTRQYFTVTN.

The ligand binding domain can be a native or wild type protein or naturally occurring alleles and splice variants, such as the extracellular domains of the receptors described herein. The ligand binding domain can be a fragment of a native sequence.

Were two or more ligand binding domains are required for binding, or selective binding, to the desirable ligand, that the natively outward faces of the ligand binding domains be preserved in selecting the linker moieties.

One of ordinary skill may select variants of a receptor by consulting the literature. For example, the human interferon gamma receptor has been well characterized with variants available in a database. See, for example, van de Vosse E, van Dissel J T (2017). "*IFN-γR1 defects: Mutation update and description of the IFNGR1 variation database*". Human Mutation. 38 (10): 1286-1296. See also, Aguet et al., "Molecular cloning and expression of the human interferon-gamma receptor" Cell 55 (2), 273-280 (1988); Stuber et al., "Alignment of disulfide bonds of the extracellular domain of the interferon gamma receptor and investigation of their role in biological activity", Biochemistry 32 (9), 2423-2430 (1993); Sakatsume et al., "The Jak kinases differentially associate with the alpha and beta (accessory factor) chains of the interferon gamma receptor to form a functional receptor unit capable of activating STAT transcription factors", J. Biol. Chem. 270 (29), 17528-17534 (1995); Walter et al., "Crystal structure of a complex between interferon-gamma and its soluble high-affinity receptor", Nature 376 (6537), 230-235 (1995); Sogabe et al., "Neutralizing epitopes on the extracellular interferon gamma receptor (IFNgammaR) alpha-chain characterized by homolog scanning mutagenesis and X-ray crystal structure of the A6 fab-IFNgammaR1-108 complex", J. Mol. Biol. 273 (4), 882-897 (1997); Thiel et al., "Observation of an unexpected third receptor molecule in the crystal structure of human interferon-gamma receptor complex", Structure 8 (9), 927-936 (2000); van de Wetering et al., "Functional analysis of naturally occurring amino acid substitutions in human IFN-gammaR1." Mol. Immunol. 47:1023-1030(2010). IL2RG structure is described in, e.g., Takeshita et al., "Cloning of the gamma chain of the human IL-2 receptor", Science 257 (5068), 379-382 (1992); Ratthe et al., "Interleukin-15 enhances human neutrophil phagocytosis by a Syk-dependent mechanism: importance of the IL-15Ralpha chain", J. Leukoc. Biol. 76 (1), 162-168 (2004); Bamborough et al., "The interleukin-2 and interleukin-4 receptors studied by molecular modelling", Structure 2 (9), 839-851 (1994); Wang et al., "Structure of the quaternary complex of interleukin-2 with its alpha, beta, and gamma receptors" Science 310 (5751), 1159-1163 (2005); Stauber et al., "Crystal structure of the IL-2 signaling complex: paradigm for a heterotrimeric cytokine receptor", Proc. Natl. Acad. Sci. U.S.A. 103 (8), 2788-2793 (2006) Variants of ILR6 are described in e.g., Yamasaki et al., "Cloning and expression of the human interleukin-6 (BSF-2/IFN beta 2) receptor" Science 241 (4867), 825-828 (1988); Buk et al., "Increased association with detergent-resistant membranes/lipid rafts of apically targeted mutants of the interleukin-6 receptor gp80" Eur. J. Cell Biol. 84 (10), 819-831 (2005); Yawata et al., Structure-function analysis of human IL-6 receptor: dissociation of amino acid residues required for IL-6-binding and for IL-6 signal transduction through gp130" EMBO J. 12 (4), 1705-1712 (1993); Horiuchi et al., "Soluble interleukin-6 receptors released from T cell or granulocyte/macrophage cell lines and human peripheral blood mononuclear cells are generated through an alternative splicing mechanism" Eur. J. Immunol. 24 (8), 1945-1948 (1994); Boulanger et al., "Hexameric structure and assembly of the interleukin-6/IL-6 alpha-receptor/gp130 complex", Science 300 (5628), 2101-2104 (2003). IL-12A is described in, e.g., Wolf et al., "Cloning of cDNA for natural killer cell stimulatory factor, a heterodimeric cytokine with multiple biologic effects on T and natural killer cells", J. Immunol. 146 (9), 3074-3081 (1991); Devergne et al., "Epstein-Barr virus-induced gene 3 and the p35 subunit of interleukin 12 form a novel heterodimeric hematopoietin", Proc. Natl. Acad. Sci. U.S.A. 94 (22), 12041-12046 (1997); Yoon et al., "Charged residues dominate a unique interlocking topography in the heterodimeric cytokine interleukin-12", EMBO J. 19 (14), 3530-3541 (2000). IL-27B is described in, e.g., Devergne "Epstein-Barr virus-induced gene 3 and the p35 subunit of interleukin 12 form a novel heterodimeric hematopoietin", Proc. Natl. Acad. Sci. U.S.A. 94 (22), 12041-12046 (1997); Pflanz et al., "IL-27, a heterodimeric cytokine composed of EBI3 and p28 protein, induces proliferation of naive CD4+ T cells", Immunity 16 (6), 779-790 (2002); Batten and Ghilardi "The biology and therapeutic potential of interleukin 27", J. Mol. Med. 85 (7), 661-672 (2007). IL-21r is described in, e.g., Ozaki et al., "Cloning of a type I cytokine receptor most related to the IL-2 receptor beta chain", Proc. Natl. Acad. Sci. U.S.A. 97 (21), 11439-11444 (2000); Kotlarz et al., "Loss-of-function mutations in the IL-21 receptor gene cause a primary immunodeficiency syndrome" J. Exp. Med. 210 (3), 433-443 (2013); Hamming et al., "Crystal structure of interleukin-21 receptor (IL-21R) bound to IL-21 reveals that sugar chain interacting with WSXWS motif is integral part of IL-21R" J. Biol. Chem. 287 (12), 9454-9460 (2012).

In various embodiments, the present heterodimeric protein may comprise an amino acid sequence having one or more amino acid mutations relative to any of the known protein sequences. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt alpha-helices.

As used herein, "non-conservative substitutions" are defined as exchanges of an amino acid by another amino acid listed in a different group of the six standard amino acid groups (1) to (6) shown above. QTY substitutions are clearly "non-conservative substitutions", the substitutions are from hydrophobic to hydrophilic without introducing any charges.

In various embodiments, the substitutions may also include non-classical amino acids (e.g., selenocysteine, pyrrolysine, N-formylmethionine .beta.-alanine, GABA and .delta.-Aminolevulinic acid, 4-aminobenzoic acid (PABA), D-isomers of the common amino acids, 2,4-diaminobutyric acid, alpha-amino isobutyric acid, 4-aminobutyric acid, Abu, 2-amino butyric acid, gamma-Abu, epsilon-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, beta-alanine, fluoro-amino acids, designer amino acids such as beta methyl amino acids, C alpha-methyl amino acids, N alpha-methyl amino acids, and amino acid analogs in general).

Mutations may also be made to the nucleotide sequences of the heterodimeric proteins by reference to the genetic code, including taking into account codon degeneracy.

In various embodiments, the present heterodimeric proteins may comprises variants of any of the known extracellular domains, for instance, a sequence having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the known amino acid or nucleic acid sequences. In embodiments, a ligand binding domain can differ from a wild type sequence, or parent protein, by 1, 2, 3, 4, 5, 6, 7, 8, 9, 10 or more amino acid substitutions.

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Fc Domain

The Fc domain of the fusion protein comprises at least a portion of a constant immunoglobulin domain, e.g., a constant heavy immunoglobulin domain or a constant light immunoglobulin domain. Preferably, the second domain comprises at least a portion of a constant heavy immunoglobulin domain. The constant heavy immunoglobulin domain is preferably an Fc fragment comprising the CH2 and CH3 domain and, optionally, at least a part of the hinge region. The immunoglobulin domain may be an IgG, IgD, IgE, IgA, or IgM, immunoglobulin domain or a modified immunoglobulin domain derived therefrom. Preferably, the second domain comprises at least a portion of a constant IgG immunoglobulin domain. The IgG immunoglobulin domain may be selected from IgG1, IgG2, IgG3 of IgG4 domains or from modified domains such as are described in U.S. Pat. No. 5,925,734.

The Fc Domain is preferably a mammalian sequence, more preferably a human sequence, or a variant of a human sequence. The examples provided below illustrate a murine IgG2 Fc domain for study purposes.

Fc domain variants have been described. For example, the Fc domain can contain one or more amino acid substitutions at amino acid residue 250, 252, 254, 256, 308, 309, 311, 428, 433 or 434 (in accordance with Kabat numbering), or equivalents thereof. For example, the amino acid substitution at amino acid residue 250 is a substitution with glutamine; the amino acid substitution at amino acid residue 252 is a substitution with tyrosine, phenylalanine, tryptophan or threonine; the amino acid substitution at amino acid residue 254 is a substitution with threonine; the amino acid substitution at amino acid residue 256 is a substitution with serine, arginine, glutamine, glutamic acid, aspartic acid, or threonine; the amino acid substitution at amino acid residue 308 is a substitution with threonine; the amino acid substitution at amino acid residue 309 is a substitution with proline; the amino acid substitution at amino acid residue 311 is a substitution with serine; the amino acid substitution at amino acid residue 385 is a substitution with arginine, aspartic acid, serine, threonine, histidine, lysine, alanine or glycine; the amino acid substitution at amino acid residue 386 is a substitution with threonine, proline, aspartic acid, serine, lysine, arginine, isoleucine, or methionine; the amino acid substitution at amino acid residue 387 is a substitution with arginine, proline, histidine, serine, threonine, or alanine; the amino acid substitution at amino acid residue 389 is a substitution with proline, serine or asparagine; the amino acid substitution at amino acid residue 428 is a substitution with leucine; the amino acid substitution at amino acid residue 433 is a substitution with arginine, serine, isoleucine, proline, or glutamine; and the amino acid substitution at amino acid residue 434 is a substitution with histidine, phenylalanine, or tyrosine.

In some embodiments, the Fc domain (e.g., comprising an IgG constant region) comprises one or more mutations such as substitutions at amino acid residue 252, 254, 256, 433, 434, or 436 (in accordance with Kabat numbering). For example, the IgG constant region includes a triple M252Y/S254T/T256E mutation or YTE mutation; the IgG constant region includes a triple H433K/N434F/N436H mutation or KFH mutation; or the IgG constant region includes an YTE and KFH mutation in combination.

In some embodiments, illustrative mutations include T250Q, M428L, T307A, E380A, 1253A, H310A, M428L, H433K, N434A, N434F, N434S, and H435A and combinations thereof. Additional exemplary mutations in the IgG constant region are described, for example, in Robbie, et al., Antimicrobial Agents and Chemotherapy (2013), 57(12): 6147-6153, Dall'Acqua et al., JBC (2006), 281(33):23514-24, Dall'Acqua et al., Journal of Immunology (2002), 169: 5171-80, Ko et al. Nature (2014) 514:642-645, Grevys et al. Journal of Immunology. (2015), 194(11):5497-508, and U.S. Pat. No. 7,083,784.

The immunoglobulin domain may exhibit effector functions, particularly effector functions selected from ADCC and/or CDC. In some embodiments, however, modified immunoglobulin domains having modified, e.g., at least partially deleted, effector functions can be used.

The Fc Domain can be modified. For example, glycosylation variants can improve or serum half. Enhanced Fc fusion protein comprising an immunoglobulin Fc region or domain comprising at least one oligosaccharide can be produced by exposing the Fc fusion protein to at least one glycosyltransferase. Pegylating the Fc domain can also improve the serum half-life.

The Fc Domain can be linked to the ligand binding domain with a hinge region, derived from an antibody (e.g., of IgG, IgA, IgD, and IgE, inclusive of subclasses (e.g., IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2. In other embodiments, the linker may be derived from human IgG4 and contain one or more mutations to enhance dimerization (including S228P) or FcRn binding.

According to crystallographic studies, the immunoglobulin hinge region can be further subdivided functionally into three regions: the upper hinge region, the core region, and the lower hinge region. See Shin et al., 1992 Immunological Reviews 130:87. The upper hinge region includes amino acids from the carboxyl end of CH1 to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the CH2 domain and includes residues in CH2. The core hinge region of wild-type human IgG1 contains the sequence Cys-Pro-Pro-Cys which, when dimerized by disulfide bond formation, results in a cyclic octapeptide believed to act as a pivot, thus conferring flexibility. In various embodiments, the present linker comprises, one, or two, or three of the upper hinge region, the core region, and the lower hinge region of any antibody (e.g., of IgG, IgA, IgD, and IgE, inclusive of subclasses (e.g. IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In various embodiments, the linker of the present invention comprises one or more glycosylation sites.

In various embodiments, the Fc Domain may comprises variants of known domains, for instance, a sequence having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the known amino acid or nucleic acid sequences. In embodiments, the Fc Domain can differ from a wild type sequence, or parent protein, by 1, 2, 3, 4, 5, 6, 7, 8, 9, 10 or more amino acid substitutions.

Fc QTY TM Fusion Receptor Proteins

Non-limiting examples of polypeptides comprising an Fc region, or polypeptides to which an Fc region may be linked or fused, for modification by methods disclosed herein include Atacicept, Romiplostim, Abatacept, ACE-536, Recombinant factor VIII-Fc, ACE-011, ALT-801, AMG 386, Dulaglutide, Aflibercept, asfotase alfa, Alefacept, CVX-096, ALXN1102/ALXN1103, CSL-654, CSL-689, F-627, FP-1039, MM-111, NGR-TNF, denileukin diftitox, SL-401, PB-1046, Albiglutide, PB-1023, BMN-701, DAS-181, ID-93/GLA-SE, VAX102 (flagellin HuM2e), VAX125 (flagellin HuHa), BA-210, LY2189365, APG101, AMG 623, CNTO 528, SB 087, TRU 015, ART 621, Belatacept (BMS 224818), Briobacept (BR3-Fc), YSPSL (PSGL-Ig), ACE 031 (RAP 011), FP 1039, ALT-802, Rilonacept, Lenercept, p55, GLP-1, factor IX, factor VIIa, human serum albumin, interleukins (e.g. IL-1, IL-2, IL-3, IL-15, IL-17, IL-22), ELP, human hyaluronidase (e.g. rHuPH20), insulin, IGF-2, flagellin, Rho, GA733, CD95, nuclease protein (e.g. DNase 1, TREX 1, DNase 1L3), recombinant versions thereof, and fusion proteins comprising one or more of these polypeptides (e.g. 1, 2, 3, 4, 5, or more). The receptor can be selected from death receptors, growth factor receptors and cytokine receptors. More preferably, the receptor is selected from CD95 (APO-1; Fas), TRAIL receptors, TNF receptors, VEGF receptors, an interleukin receptor such as IL-15Rα. Most preferably the receptor is CD95, a TRAIL receptor, e.g., the TRAIL receptor-1, the TRAIL receptor-2, the TRAIL receptor-3 or the TRAIL receptor-4 or a TNF receptor, e.g., the TNF receptor-1 or the TNF receptor-2.

Vectors & Polynucleotides

In other embodiments, the application provides nucleic acids encoding any of the various Fc fusion proteins disclosed herein. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc. Natl. Acad. Sci. USA, 100(2):438-442 (Jan. 21, 2003); Sinclair et al., Protein Expr. Purif, 26(I):96-105 (October 2002); Connell, N. D., Curr. Opin. Biotechnol., 12(5):446-449 (October 2001); Makrides et al., Microbiol Rev., 60(3):512-538 (September 1996); and Sharp et at., Yeast, 7(7):657-678 (October 1991).

General techniques for nucleic acid manipulation are described for example in Sambrook et al., Molecular Cloning: A Laboratory Manual, 2nd Edition, Vols. 1-3, Cold Spring Harbor Laboratory Press (1989), or Ausubel, F. et at., Current Protocols in Molecular Biology, Green Publishing and Wiley-Interscience, New York (1987) and periodic updates, herein incorporated by reference. Generally, the DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The Fc fusion receptor proteins may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. An N-terminal leader sequence can be removed by the host cell following expression.

For prokaryotic host cells that do not recognize and process a native signal sequence, the signal sequence is substituted by a prokaryotic signal sequence selected, for example, from the group of the alkaline phosphatase, penicillinase, lpp, or heat-stable enterotoxin II leaders.

For yeast secretion the native signal sequence may be substituted by, e.g., the yeast invertase leader, a factor leader (including Saccharomyces and Kluyveromyces alpha-factor leaders), or acid phosphatase leader, the *C. albicans* glucoamylase leader, or the signal described in U.S. Pat. No. 5,631,144. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Expression and cloning vectors usually contain a promoter that is recognized by the host organism and is operably linked to the nucleic acid encoding the protein disclosed herein, e.g., a fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tan promoter. However, other known bacterial promoters are suitable. Promoters for use in bacterial systems also will contain a Shine-Dalgarno (S.D.) sequence operably linked to the DNA encoding the protein disclosed herein. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tall to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

Transcription of a DNA encoding proteins disclosed herein by higher eukaryotes is often increased by inserting an enhancer sequence into the vector. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature, 297:17-18 (1982) on enhancing elements for activation of eukaryotic promoters. The enhancer may be spliced into the vector at a position 5' or 3' to the peptide-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of mRNA encoding the protein disclosed herein. One useful transcription termination component is the bovine growth hormone polyadenylation region. See WO94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, Rho tag, Strep tag or a GST tag. Appropriate cloning and expression vectors for use with bacterial, fungal, yeast, and mammalian cellular hosts can be found in Cloning Vectors: A Laboratory Manual, (Elsevier, N.Y. (1985)), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram-positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow et al. (Bio/Technology, 6:47 (1988)). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Receptor Protein Production

Host cells containing vectors encoding the Fc fusion receptor proteins described herein, as well as methods for producing the Fc fusion receptor proteins are described herein. Host cells may be transformed with the herein-described expression or cloning vectors for protein production and cultured in conventional nutrient media modified as appropriate for inducing promoters, selecting transformants, or amplifying the genes encoding the desired sequences. Host cells useful for high-throughput protein production (HTPP) and mid-scale production include the HMS174-bacterial strain. The host cells used to produce the proteins disclosed herein may be cultured in a variety of media. Commercially available media such as Ham's F10 (Sigma), Minimal Essential Medium ((MEM), (Sigma)), RPM1-1640 (Sigma), and Dulbecco's Modified Eagle's Medium ((DMEM), Sigma)) are suitable for culturing the host cells. In addition, many of the media described in Ham et al., Meth. Enzymol., 58:44 (1979), Barites et al., Anal. Biochem., 102:255 (1980), U.S. Pat. Nos. 4,767,704, 4,657, 866, 4,927,762, 4,560,655, 5,122,469, 6,048,728, 5,672,502, or U.S. Pat. No. RE 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The Fc fusion receptor proteins provided herein can also be produced using cell-free translation systems. For such purposes the nucleic acids encoding the fusion protein must be modified to allow in vitro transcription to produce mRNA and to allow cell-free translation of the mRNA in the particular cell-free system being utilized (eukaryotic such as a mammalian or yeast cell-free translation system or prokaryotic such as a bacterial ceil-free translation system.

The Fc fusion receptor proteins disclosed herein can also be produced by chemical synthesis (e.g., by the methods described in Solid Phase Peptide Synthesis, 2nd Edition, The Pierce Chemical Co., Rockford, Ill. (1984)). Modifications to the Fc fusion receptor proteins can also be produced by chemical synthesis.

The Fc fusion receptor proteins disclosed herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, get filtration, gel permeation chromatography, affinity chromatography, electrophoresis, counter-currant distribution or any combinations of these. After purification, polypeptides may be exchanged into different buffers and/or concentrated by any of a variety of methods known to the art, including, but not limited to, filtration and dialysis.

The purified Fc fusion proteins are preferably at least 85% pure, or preferably at least 95% pure, and most preferably at least 98% pure. Regardless of the exact numerical value of the purity, the Fc fusion protein is sufficiently pure for use as a pharmaceutical product.

QTY Design

In some aspects, the invention is directed to the use of the QTY (Glutamine, threonine and tyrosine) replacement (or "Code") method (or "principle") to change the transmembrane α-helix hydrophobic residues leucine (L), isoleucine (I), valine (V), and phenylalanine (F) of a native protein to the hydrophilic residues glutamine (Q), threonine (T) and tyrosine (Y), or alternatively, as described above, Asn (N) and Ser (S) for L, I and/or V. This invention can convert a water insoluble, native membrane protein to a water-soluble counterpart.

Herein the applicants reported the QTY code design of several cytokine receptors including 2 variants of interleukin receptors IL4R and IL10R, as well as 2 variants of interferon receptors IFNγR1 and IFNλR1. These QTY code designed receptors show ligand-binding properties similar to their counterpart native receptors without the presence of hydrophobic patches. The receptors were fused with Fc domain of mouse IgG2a protein to form an antibody-like structure. These Fc-fusion receptors can be expressed and purified in *E. coli* system with sufficient yield (~mg/L) in LB media. We also showed that these QTY receptors are capable to bind to their respective ligands with affinity close to isolated native receptors on solution-based assays. These QTY code design of functional, water-soluble Fc-fusion cytokine receptors can potentially be used clinically as decoy therapy to rapidly remove excessive cytokines in the setting of hyperactive immune reactions during CRS or "cytokine storm".

Both interferon receptors and interleukin receptors have a single-pass in the transmembrane domain. The ligand binding domain is typically comprised by multiple stranded β-sheets that forms two connected anti-parallel β-barrels. The β-barrels are connected to the transmembrane α-helix which is responsible for signal transduction, presumably playing a role in ligand interaction (Richter et al., 2017). In order to best mimic a native receptor, we included the transmembrane domain in our design with a few amino acids in the cytoplasmic region to serve as a short linker so as to optimize the binding and structure of the QTY code modified receptors.

Figure 1B:
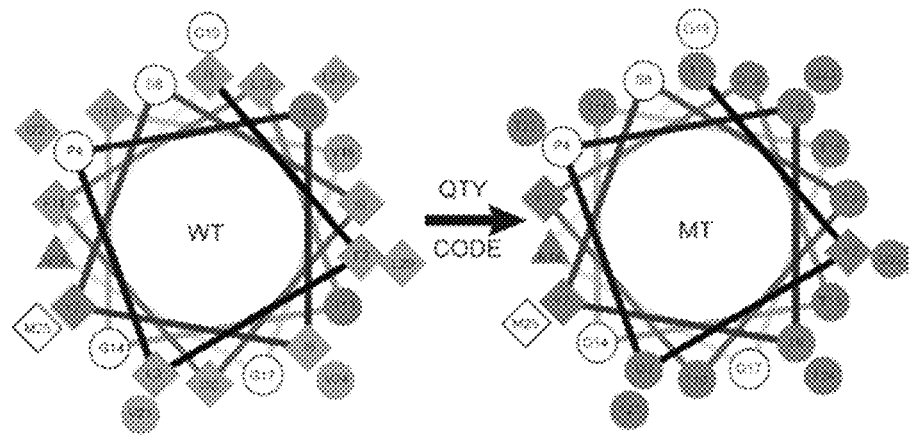
Figure 3A:
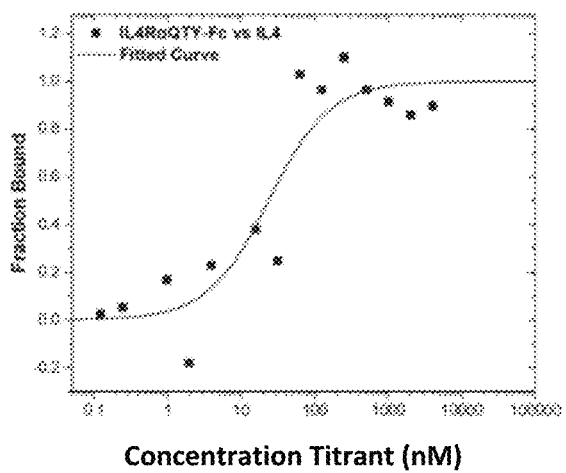
FIG. 3A-3D. MST ligand binding measurements. The receptors were labeled with fluorescent dye. The ligands were purchased commercially from and dissolved in di water.
Figure 3B:
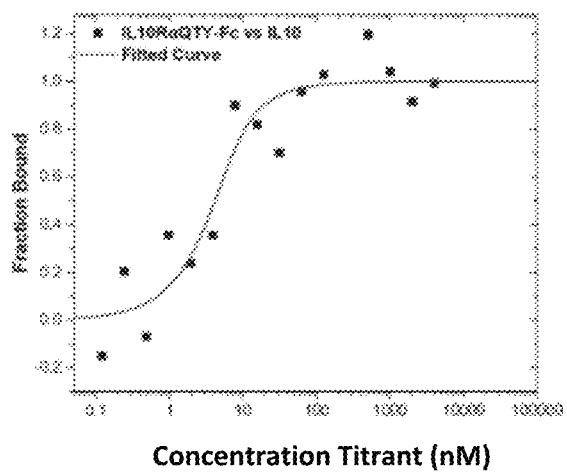
Figure 3C:
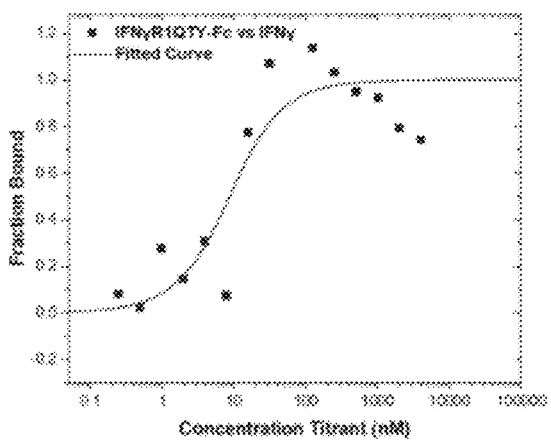
Figure 3D:
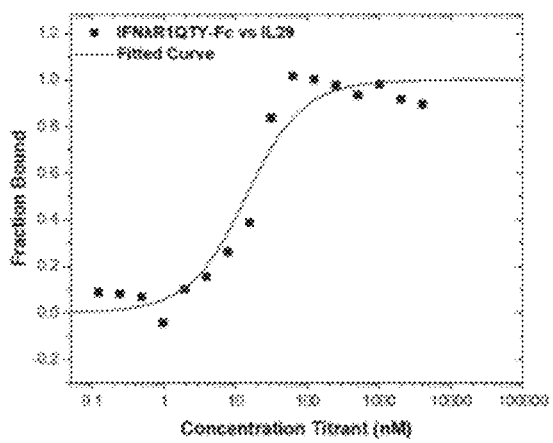

QTY code was only applied to the transmembrane domains of these receptors. Due to the relative weight of TM region, the changes in molecular weight of interferon and interleukin receptors were minimum. pI changes are 0.00, 0.02, 0.18 and 0.01 for IL4Rα$^{QTY}$, IL10Rα$^{QTY}$, IFNγR1$^{QTY}$ and IFNλR1$^{QTY}$, respectively. The larger pI change in IFNγR1$^{QTY}$ was probably due to its larger deviation towards charge neutral point as compared to other receptors as shown in FIG. 1 (5.10 for IFNγR1$^{QTY}$ compared to 6.15 for IL4Rα$^{QTY}$, 8.68 for IL10Rα$^{QTY}$ and 8.41 for IFNλR1$^{QTY}$).

The applicants specifically designed the QTY receptor variants to fuse with the Fc region of IgG protein in order to acquire an antibody-like structure, as well as to promote their antibody-like functions and properties for specific ligand recognition and binding while retaining their receptor characteristics. A spacer was introduced to optimize the conformation of QTY code designed receptors in the heavy chain. We used the Fc region of mouse IgG2a in the specific design as it is the functional equivalent of human IgG1. Mouse IgG is chosen over human IgG due to the consideration of implementing mouse cytokine storm model in subsequent experiments, which is beyond the scope of current study. The Fc region can be easily exchanged in future designs. The structural illustrations were obtained through Uniprot where applicable or from a homology model (CXCR2) (Kwon, 2010).

Bioinformatics Analysis

QTY variant protein sequences were analyzed using a web-based tool TMHMM Server v2.0 to predict the existence of hydrophobic transmembrane segments. The server is based on a Hidden Markov Model (HMM) that takes into account actual biological architectures of a transmembrane helix whereas likelihood of presence is calculated (Sonnhammer et al., 1998).

Protein hydrophobicity can be plotted versus the protein sequences. The X-axis can show the number of amino acids in sequences from N-terminus to C-terminus. In interleukin and interferon receptors, a single high probability hydrophobic segment near the C-terminus end of each receptor and are also eliminated though QTY modification. The hydrophobicity of both extracellular and intracellular components is unchanged.

*E. coli* Expression and Gel-Electrophoresis of QTY Variant Receptors

The corresponding genes with *E. coli* specific codons were synthesized and expressed in sufficient quantities. The throughput for each receptor differed but was all in mg/L range in LB media. All Fc fusion receptors were expressed into inclusion bodies. They were purified by a) affinity purification, and b) gel filtration in denatured state and then folded into functional state for subsequent analysis. Both arginine and DTT were beneficial for solubilizing the proteins so either or both of them were included in the storage buffer or for ligand binding tests.

Interleukin and interferon receptors exhibited monomer bands on gel electrophoresis that corresponded well with their respective molecular weight.

Bold denotes transmembrane region of a receptor, within which, dark magenta denotes QTY substitution. Underlined parts are tags and restriction sites used for purification and future swapping of the Fc region for tests in respective animals. Italicized sequence corresponds to the Fc region of IgG protein, where in this case, is mouse IgG2a-Fc, the functional equivalent of human IgG1. The hinge region has the sequence PRGPTIKPCPPCKCPAPNLLGGP (SEQ ID NO. 16), following the underlined sequences.

```
1) HUMAN Interferon gamma receptor 1-Fc fusion
                                                 SEQ ID NO. 11
MALLFLLPLVMQGVSRAEMGTADLGPSSVPTPTNVTIESYNMNPIVYWEYQIMPQVPVF

TVEVKNYGVKNSEWIDACINISHEYCNISDHVGDPSNSLWVRVKARVGQKESAYAKSEE

FAVCRDGKIGPPKLDIRKEEKQIMIDIFHPSVFVNGDEQEVDYDPETTCYIRVYNVYVR

MNGSEIQYKILTQKEDDCDEIQCQLAIPVSSLNSQYCVSAEGVLHVWGVTTEKSKEVCI

TIFNSSIKGSQWTPTTAAQQQYQTQSQTYTCFYIKKTETSQVAPAHHHHHHHHHGSKL

VDPRGPTIKPCPPCKCPAPNLLGGPSVFIFPPKIKDVLMISLSPIVTCVVVDVSEDDPD

VQISWFVNNVEVHTAQTQTHREDYNSTLRVVSALPIQHQDWMSGKEFKCKVNNKDLPAP

IERTISKPKGSVRAPQVYVLPPPEEEMTKKQVTLTCMVTDFMPEDIYVEWTNNGKTELN

YKNTEPVLDSDGSYFMYSKLRVEKKNWVERNSYSCSVVHEGLHNHHTTKSFSRTPGK.
```

-continued

2) HUMAN Interferon gamma receptor 2-Fc fusion
SEQ ID NO. 12

MRPTLLWSLLLLLGVFAAAAAAPPDPLSQLPAPQHPKIRLYNAEQVLSWEPVALSNSTR

PVVYQVQFKYTDSKWFTADEVISIGVNCTQITATECDFTAASPSAGFPMDFNVTLRLRA

ELGALHSAWVTMPWFQHYRNVTVGPPENIEVTPGEGSLIIRFSSPFDIADTSTAFFCYY

VHYWEKGGIQQVKGPFRSNSISLDNLKPSRVYCLQVQAQLLWNKSNIFRVGHLSNISCY

ETMADASTELQQTTQTSTGTYSQQSTQAGACYYQTQKYRG<u>TETSQVAPAHHHHHHHHH</u>

<u>GSKLVD</u>*PRGPTIKPCPPCKCPAPNLLGGPSVFIFPPKIKDVLMISLSPIVTCVVVDVSE*

*DDPDVQISWFVNNVEVHTAQTQTHREDYNSTLRVVSALPIQHQDWMSGKEFKCKVNNKD*

*LPAPIERTISKPKGSVRAPQVYVLPPPEEEMTKKQVTLTCMVTDFMPEDIYVEWTNNGK*

*TELNYKNTEPVLDSDGSYFMYSKLRVEKKNWVERNSYSCSVVHEGLHNHHTTKSFSRTP*

*GK.*

3) HUMAN Interferon lambda receptor 1-Fc fusion
SEQ ID NO. 13

MAGPERWGPLLLCLLQAAPGRPRLAPPQNVTLLSQNFSVYLTWLPGLGNPQDVTYFVAY

QSSPTRRRWREVEECAGTKELLCSMIVICLKKQDLYNKFKGRVRTVSPSSKSPWVESEY

LDYLFEVEPAPPVLVLTQTEEILSANATYQLPPCMPPLDLKYEVAFWKEGAGNKTLFPV

TPHGQPVQITLQPAASEHHCLSARTIYTFSVPKYSKFSKPTCFLLEVPEANWAYQTQPS

QQTQQQTTAAGGTTWKTLMGN<u>TETSQVAPAHHHHHHHHHGSKLVD</u>*PRGPTIKPCPPCK*

*CPAPNLLGGPSVFIFPPKIKDVLMISLSPIVTCVVVDVSEDDPDVQISWFVNNVEVHTA*

*QTQTHREDYNSTLRVVSALPIQHQDWMSGKEFKCKVNNKDLPAPIERTISKPKGSVRAP*

*QVYVLPPPEEEMTKKQVTLTCMVTDFMPEDIYVEWTNNGKTELNYKNTEPVLDSDGSYF*

*MYSKLRVEKKNWVERNSYSCSVVHEGLHNHHTTKSFSRTPGK.*

4) HUMAN Interleukin-4 receptor subunit alpha-Fc fusion
SEQ ID NO. 14

MGWLCSGLLFPVSCLVLLQVASSGNMKVLQEPTCVSDYMSISTCEWKMNGPTNCSTELR

LLYQLVFLLSEAHTCIPENNGGAGCVCHLLMDDVVSADNYTLDLWAGQQLLWKGSFKPS

EHVKPRAPGNLTVHTNVSDTLLLTWSNPYPPDNYLYNHLTYAVNIWSENDPADFRIYNV

TYLEPSLRIAASTLKSGISYRARVRAWAQCYNTTWSEWSPSTKWHNSYREPFEQHQQQG

TSTSCTTTQATCQQCYTSTTKIKKE<u>TETSQVAPAHHHHHHHHHGSKLVD</u>*PRGPTIKPC*

*PPCKCPAPNLLGGPSVFIFPPKIKDVLMISLSPIVTCVVVDVSEDDPDVQISWFVNNVE*

*VHTAQTQTHREDYNSTLRVVSALPIQHQDWMSGKEFKCKVNNKDLPAPIERTISKPKGS*

*VRAPQVYVLPPPEEEMTKKQVTLTCMVTDFMPEDIYVEWTNNGKTEL1VYKNTEPVLDS*

*DGSYFMYSKLRVEKKNWVERNSYSCSVVHEGLHNHHTTKSFSRTPGK.*

5) HUMAN Interleukin-10 receptor subunit alpha-Fc fusion
SEQ ID NO. 15

MLPCLVVLLAALLSLRLGSDAHGTELPSPPSVWFEAEFFHHILHWTPIPNQSESTCYEV

ALLRYGIESWNSISNCSQTLSYDLTAVTLDLYHSNGYRARVRAVDGSRHSNWTVTNTRF

SVDEVTLTVGSVNLEIHNGFILGKIQLPRPKMAPANDTYESIFSHFREYEIAIRKVPGN

FTFTHKKVKHENFSLLTSGEVGEFCVQVKPSVASRSNKGMWSKEECISLTRQYFTVTNT

TTYYAYTQQQSGAQAYCQAQQLYVRRRKK<u>TETSQVAPAHHHHHHHHHGSKLVD</u>*PRGPT*

*IKPCPPCKCPAPNLLGGPSVFIFPPKIKDVLMISLSPIVTCVVVDVSEDDPDVQISWFV*

*NNVEVHTAQTQTHREDYNSTLRVVSALPIQHQDWMSGKEFKCKVNNKDLPAPIERTISK*

-continued

PKGSVRAPQVYVLPPPEEEMTKKQVTLTCMVTDTMPEDIYVEWTNNGKTELNYKNTEPV

LDSDGSYFMYSKLRVEKKNWVERNSYSCSVVHEGLHNHHTTKSFSRTPGK.

Ligand-Binding Measurement in Buffer

The affinity of QTY modified cytokine receptor fused with Fc of IgG for their respective native ligands was measured using MicroScale Thermophoresis (MST). Changes in thermophoretic movement for labeled proteins upon ligand-binding were recorded and plotted as a function of ligand concentration. Both QTY code designed Fc-fusion interleukin and interferon receptors showed no non-specific adhesion or aggregation during the measurement.

QTY Fc-fusion receptors exhibit affinity for their respective ligands typically in nM to tens of nM range (Table 1). The affinities are lower compared to the native receptors without Fc-fusion. For affinities of interleukin and interferon receptors, previous reported studies primarily used human neutrophils cell-based assay with isotope $^{125}$I-labeled ligand that is significantly more sensitive than using the purified receptors measured by biophysical instrument, thus they may not be directly comparable. The affinity $K_d$ derived from MST displays similar values compared to previous SPR measurement on purified proteins with the exception of IL4R$^{QTY}$-Fc. The method that was used to determine the $K_d$ in literature was also included in Table.

TABLE

Ligand-binding affinity of Fc fused QTY cytokine receptors

|  | Native ($K_d$, nM) | QTY variant ($K_d$, nM) |
|---|---|---|
| IL4Rα$^{QTY}$-Fc vs IL4 | ~1 nM (SPR) (LaPorte et al., 2008) | 20.9 ± 8.3 |
| IL10Rα$^{QTY}$-Fc vs IL10 | 0.05-0.2 (Cell) (Tan etal., 1993) | 1.6 ± 0.9 |
| IFNγR1$^{QTY}$-Fc vs IFNγ | 1.7 (Cell) (Celada et al., 1985) 30.8 (SPR) (Mikulecky et al., 2013) | 6.2 ± 3.0 |
| IFNλR1$^{QTY}$-Fc vs IL29 | — | 11.5 ± 2.5 |

The applicants' Fc-fusion water-soluble receptors, as a decoy, can rapidly soak up excessive cytokines during "cytokine storm" unleashed during CAR-T treatment and COVID-19. When the designed water-soluble Fc-receptors bind to excessive cytokines, they act as decoy to prevent the excessive cytokine to directly interact with target cells, therefore reduce the organ damage and toxicity conferred by "cytokine storm". There are over 20 Fc-fusion proteins commercially available and several of these have been developed as therapeutics (Czajkowsky et al., 2012). Although there have been many Fc-fusion proteins developed for various applications, they are water-soluble proteins (Czajkowsky et al., 2012; Mekhaiel et al., 2011). The applicants' QTY code designed Fc-fusion receptors provide a novel platform for further design of other types of fusion membrane receptors for therapeutic and diagnostic applications.

The design and synthesis of functionally equivalent transmembrane proteins have implications beyond biological and clinical use. Highly specific towards their respective ligands, QTY code modified transmembrane proteins can also serve as ideal candidates for molecular sensing. Complex electrical arrays functionalized with a variety types of water-soluble membrane proteins can potentially mimic cell response in vitro and be fabricated into a pseudo cell with electrical readouts.

Materials and Methods

Genes Identification and QTY Modification

Sequences of the respective proteins were obtained from Uniprot: www.uniprot.org/. Respective extracellular, transmembrane and cytoplasmic domains were identified. QTY code was only applied to the transmembrane helical domain to solubilize the proteins.

Bioinformatics Analysis

Protein properties were calculated based on their primary sequences via the open access web-based tool ExPASy: web.expasy.org/protparam. The existence of hydrophobic patch within the transmembrane region in native and QTY variant protein sequences was determined via the open access web-based tool TMHMM Server v.2.0: www.cbs.dtu.dk/services/TMHMM-2.

E. coli Expression System and Protein Purification

Genes of QTY modified cytokine receptor proteins were cloned into Fc region of mouse IgG2a which is the functional equivalence of human IgG1. The full sequences were codon optimized for E. coli expression and obtained from Genscript. The genes were cloned into pET20b expression vector with Carbenicillin resistance. The plasmids were reconstituted and transformed into E. coli BL21(DE3) strain. Transformants were selected on LB medium plates with 100 μg/ml Carbenicillin. E. coli cultures were grown at 37° C. until the OD$_{600}$ reached 0.4-0.8, after which IPTG (isopropyl-D-thiogalactoside) was added to a final concentration of 1 mM followed by 4-hour expression. Cells were lysed by sonication in B-PER™ protein extraction agent (Thermos-Fisher) and centrifuged (23,000×g, 40 min, 4° C.) to collect the inclusion body. The biomass was then subsequently washed twice in buffer 1 (50 mM Tris.HCl pH7.4, 50 mM NaCl, 10 mM CaCl2, 0.1% v/v Trition X100, 2M Urea, 0.2 μm filtered), once in buffer 2 (50 mM Tris.HCl pH7.4, 1M NaCl, 10 mM CaCl2, 0.1% v/v Trition X100, 2M Urea, 0.2 μm filtered) and again in buffer 1. Pellets from each washing step were collected by centrifugation (23,000×g, 25 min, 4° C.).

Washed inclusion bodies were fully solubilized in denaturation buffer (6M guanidine hydrochloride, 1×PBS, 10 mM DTT, 0.2 μm filtered) at room temperature for 1.5 hour with magnetic stirring. The solution was centrifuged at 23,000×g for 40 min at 4° C. The supernatant with proteins was then purified by Qiagen Ni-NTA beads (His-tag) followed by size exclusion chromatography using an AKTA Purifier system and a GE healthcare Superdex 200 gel-filtration column. Purified protein was collected and dialyzed twice against renaturation buffer (50 mM Tris. HCl pH 9.0, 3 mM reduced glutathione, 1 mM oxidized glutathione, 5 mM ethylenediaminetetraacetic acid, and 0.5M L-arginine). Following an overnight refolding process, the re-natured protein solution was dialyzed into storage buffer of 50 mM Tris. HCl pH 9.0 with various arginine content.

Microscale Thermophoresis

MicroScale Thermophoresis (MST) is an optical method detecting changes in thermophoretic movement and TRIC of the protein-attached fluorophore upon ligand binding. Active labelled proteins contribute to the thermophoresis signal upon ligand binding. Inactive proteins influence the data as background but not the signals and only data from binding proteins are used to derive the $K_d$ value. Herein ligand binding experiments were carried out with 5 nM NT647-labeled protein in 1×PBS, 10 mM DTT buffer with different concentration of arginine, against a gradient of respective ligands on a Monolith NT.115 pico instrument at 25° C. Synthesized receptors were labeled with Monolith NT™ $2^{nd}$ generation protein labeling kit RED-NHS (NanoTemper Technologies) so as to obtain unique fluorescent signals. MST time traces were recorded and analyzed to obtain the highest possible signal-to-noise levels and amplitudes, >5 Fnorm units. The recorded fluorescence was plotted against the concentration of ligand, and curve fitting was performed using the $K_d$ fit formula derived from the law of mass action. For clarity, binding graphs of each independent experiment were normalized to the fraction bound (0=unbound, 1=bound). MST experiments were performed in the Center for Macromolecular Interactions at Harvard Medical School.

$K_d$ Fitting Model:

$K_d$ model is the standard fitting model based on law of mass action.

Curve fit formula:

$$F(c_T) = F_u + (F_b - F_u) * \frac{c_{AT}}{c_A}$$

$$\frac{c_{AT}}{c_A} = \text{fraction bound} = \frac{1}{2c_A} * \left(c_T + c_A + K_D - \sqrt{(c_T + c_A + K_D)^2 - 4c_T c_A}\right)$$

$F_u$: fluorescence in unbound state
$F_b$: fluorescence in bound state
$K_D$: dissociation constant, to be determined
$c_{AT}$: concentration of formed complex
$c_A$: constant concentration of molecule A (fluorescent), known
$c_T$: concentration of molecule T in serial dilution.

In broad terms, the protein design process comprises all, or substantially all, the steps:

(1) identifying a first transmembrane region by predicting an alpha-helical structure of a protein;
(2) modifying a plurality of hydrophobic amino acids via the QTY Code, as defined herein to obtain a modified first transmembrane sequence;
(3) scoring the propensity of the alpha-helical structure of the first modified transmembrane sequence of (2) to arrive at a structure score;
(4) scoring the water solubility prediction of the first modified transmembrane sequence of (2) to arrive at a solubility score;
(5) repeating steps (2) through (4) to arrive at a first library of putative water soluble first modified transmembrane variants;
(6) comparing the structure scores and solubility scores of each putative water soluble first modified transmembrane variants in the first library and, preferably ranking the putative water soluble first modified transmembrane variants using said structure scores and solubility scores;
(7) selecting a plurality of putative water soluble first modified transmembrane variants (wherein the plurality is the integer, H, or preferably less than 10, 9, 8, 7, 6, 5 or 4) to arrive at a second library of putative water soluble first modified transmembrane variants;
(8) optionally repeating steps (1) through (7) for a subsequent transmembrane regions of the protein (including a second subunit, the sum of the transmembrane regions modified by the method being the integer n);
(9) identifying the amino acid sequences of the protein which are not included in any transmembrane region modified in steps (1) through (8), and including any ligand binding region or extracellular domain of the protein; and
(10) identifying a nucleic acid sequence for each putative water soluble modified transmembrane variant and each amino acid sequence identified in step (9).

Using the nucleic acid sequences identified in the above process, nucleic acid sequences for each putative water-soluble modified transmembrane variant and each non-transmembrane domains (including the extracellular domains) can be generated and combinatorially expressed to design a library of up to $H^n$ putative water-soluble protein variants. For example, where H is 8 and n is 7, a library of approximately 2 million water-soluble protein variants can be designed.

The method provides for "scoring" the domains' including the propensity to form an alpha helix and water solubility prediction. As one of ordinary skill in the art would appreciate, the domains having different sequences will likely predict different water solubilities and propensities for alpha helical formation. One can assign "a score" to a specific predicted water solubility or range of solubilities, propensity to form alpha helical structure or range of propensities. The score can be qualitative (0,1) where 0 can represent, for example, a domain with an unacceptable predicted water solubility and 1 can represent, for example, a domain with an acceptable predicted water solubility. Or, the score can be assessed on a scale, for example, between 1 and 10 establishing characterizing increasing degrees of water solubility. Or, the score can be quantitative, such as in describing the predicted solubility in terms of mg/ml. Upon assessing a score to each domain, the domain variants can be readily compared (or ranked) by one or, preferably, both of the scores to select domain variants that will likely be both water soluble and form alpha helices.

Step-by-Step Description:

1: In step 1, a computer interface of a computer system receives a protein sequence, selected for analysis, and data descriptive of the protein (e.g., the sequence) entered, uploaded or inputted through a computer interface of a computer system. The data entered can be a protein name, a database reference, or a protein sequence. For example, the protein sequence can be uploaded through a computer interface.

2: In step 2, additional data about the protein can be identified, determined, obtained and/or entered, including its name or sequence and entered via the computer interface. One source to obtain protein data is a database named UniProt (www.uniprot.org/). Alternatively, the method of the invention can store data relating to the protein, or related sequences to the protein, for later retrieval by the user in this step. In embodiments, the program can prompt the user to select a database or file for retrieving additional data (e.g., sequence data) relating to the protein selected for analysis.

3: In step 3, the user can enter, upload, or obtain data identifying the transmembrane regions. For example, the user can be prompted to obtain the data from a public source, such as from UniProt. The information can be collected from the database for use in Step 5.

4: Alternatively or additionally, the transmembrane region can be predicted by the method. Transmembrane regions are generally characterized by an alpha helical conformation. Transmembrane helix prediction can be predicted using a software package named TMHMM 2.0 (TransMembrane prediction using Hidden Markov Models), developed by Center for Biological Sequence Analysis (http://www.cbs.dtu.dk/services/TMHMM). Some versions of the software have some problems on peak finding and sometimes fails to find TM regions. Therefore, in a preferred embodiment, a modified version of the program is used, wherein the peak searching method execute by the computer system introduces a dynamic baseline. Here, if the TMs using the initial baseline value are not found, the baseline can be changed to a lower value. For example, the default baseline is 0.2. One can set the baseline value to 0.1. If too many TMs are found, the baseline can be changed to a higher value, such as 0.15.

5: After identifying the TM data in the form, the sequence of a protein is divided into fragments including transmembrane segments and non-transmembrane segments.

It is understood that the system can execute one or more, such as all of the steps described above, using a computer interface for input by a user.

A first transmembrane region (typically, but not essentially, the transmembrane region which is most proximal to the N-terminal of the protein) is selected for variation. Hydrophobic amino acids (L, I, V, and F) are then substituted with the corresponding hydrophilic amino acid (Q, T or Y). It is understood that the amino acid is not actually substituted into the protein, in this context. Rather, the amino acid designation is substituted in the sequence for modeling. Thus, the term "sequence" is intended to include "sequence data." Typically, most or all of the hydrophobic amino acids are selected for substitution. If less than all amino acids are selected, it may be desirable to select the internal hydrophobic amino acids leaving one or more N and/or C terminal amino acids of the transmembrane regions hydrophobic. Additionally or alternatively, it may be desirable to select to replace all of the leucines (L) in a transmembrane region. Additionally or alternatively, it may be desirable to select to replace all of the isoleucines (I) in a transmembrane region. Additionally or alternatively, it may be desirable to select to replace all of the valines (V) in a transmembrane region. Additionally or alternatively, it may be desirable to select to replace all of the phenylalanines (F) in a transmembrane region. Additionally or alternatively, it can be beneficial to retain one or more phenylalanines in the transmembrane region. Additionally or alternatively, it can be beneficial to retain one or more valines in the transmembrane region. Additionally or alternatively, it can be beneficial to retain one or more leucine in the transmembrane region. Additionally or alternatively, it can be beneficial to retain one or more isoleucines in the transmembrane region. Additionally or alternatively, it can be beneficial to retain one or more hydrophobic amino acids in the transmembrane region where the wild type sequence is characterized by three or more contiguous hydrophobic amino acids. The transmembrane region so designed (the transmembrane variant or "variant") is then subjected to the transmembrane region prediction process, as discussed herein. The variant is then assessed a score for the sequence's propensity to form an alpha helix. The variant is also subjected to a water solubility prediction process, as discussed herein. The variant is assessed a score for the sequence's propensity to be water soluble. Of course, complete water solubility at all concentrations is not required for most commercial purposes. Water solubility is preferably determined to be that required for functionality at the predicted conditions of use (e.g., in a ligand binding assay).

Variants that predict loss of alpha helical structure and/or "water insolubility" (predicted at the expected conditions of use) are discarded. Variants that predict alpha helical structure and water solubility can be selected. One can select transmembrane variants that are highly water soluble, or are characterized by 0, 1, 2, or 3 hydrophobic amino acids, with a possible expectation that alpha helical structure can be compromised. Alternatively or additionally, one can select highly alpha-helical structures, characterized by 3, 4, 5 or 6 hydrophobic amino acids. These steps can be repeated for a second, third, fourth, fifth, sixth and/or seventh (or more) transmembrane region or domain.

One can select a combination of each domain where one, two, three or four domain variants possess high alpha-helical structure scores and one, two, three, four, five or six domain variants possess high water solubility scores. For example, one can choose a domain that is characterized by all hydrophobic amino acids being substituted by a hydrophilic amino acid, maximizing the water solubility score and a second domain variant selection that retains 3, 4, or 5 hydrophobic amino acids in a plurality of variant selections. Selected variants are then "shuffled," as is known in the art, with the extracellular and intracellular domains to create an initial library of putative water-soluble protein variants.

All or a fraction of the putative water-soluble protein variants of the initial library designed as described herein can be made and screened for water solubility and/or ligand binding, preferably in a high through-put screen. Amplification of the library, for example, can result in less than 100% of the putative water-soluble protein variants from being expressed. A reporter system can be used to screen ligand binding, as is well known in the art. Using the methods of the invention, one can rapidly identify a library of putative water soluble modified transmembrane variants that, when functionally combined with the extracellular and intracellular domains, will generate water soluble protein variants possessing the proper 3-dimensional structure of the wild type protein, to retain ligand binding function (including binding affinity), or other functions.

A theoretical initial library of all possible water-soluble variants can be made. Smaller libraries are preferred and can be optimized using routine experimentation based on analysis of the research results as described herein. Analysis of research results is likely to establish trends to optimize the number of domain variants to shuffle and the assumptions for selecting domain variants. Targeting transmembrane regions, we selected the amino acids for modifying based on the helical forming propensity also known as "the helix prediction score." www.proteopedia.org/wiki/index.php/Main_Page. The varied fragments are randomly assembled to form about 2M ($8^7$) variants of full-length GPCR genes. The predicted number of variants can be characterized by the formula $H^n$, where n=the number of transmembrane regions modified and/or varied by the method (in this example, 7) and H=number of variants in each transmembrane region.

Once the initial library, or selection of the domain variants to be shuffled, is selected, nucleic acid molecules, or DNA or cDNA molecules, encoding the proteins in the initial library can be designed. The nucleic acid molecules are preferably designed to provide codon optimization and intron deletions for the expression systems selected to produce a library of coding sequences. For example, if the expression system is *E. coli*, codons optimized for *E. coli* expression can be selected. www.dna20.com/resources/genedesigner. In addition, a promoter region, such as a promoter suitable for expression in the expression system (e.g., *E. coli*) is selected and operatively connected to the coding sequences in the library of coding sequences.

The initial library of coding sequences, or a portion thereof, is then expressed to produce a library of proteins. The library is then subjected to a ligand binding assay. In the binding assay, fusion proteins are contacted with the ligand, preferably in an aqueous medium and ligand binding is detected.

The invention includes transmembrane domain variants, and nucleic acid molecules encoding same, obtained, or obtainable, from the methods described herein.

The invention further encompasses a method of treatment for a disorder or disease that is mediated by the activity of a membrane protein, comprising the use of a water-soluble polypeptide to treat said disorders and diseases, wherein said water-soluble polypeptide comprises a modified α-helical domain, and wherein said water-soluble polypeptide retains the ligand-binding activity of the native membrane protein. Examples of such disorders and diseases include, but are not limited to, cancer, small cell lung cancer, melanoma, breast cancer, Parkinson's disease, cardiovascular disease, hypertension, and asthma.

As described herein, the water-soluble peptides described herein can be used for the treatment of conditions or diseases mediated by the activity of a membrane protein. In certain aspects, the water-soluble peptides can act as "decoys" for the membrane receptor and bind to the ligand that otherwise activates the membrane receptor. As such, the water-soluble peptides described herein can be used to reduce the activity of a membrane protein. These water-soluble peptides can remain in the circulation and competitively bind to specific ligands, thereby reducing the activity of membrane bound receptors.

The invention also encompasses a pharmaceutical composition comprising said water-soluble polypeptide and a pharmaceutically acceptable carrier or diluent.

The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

The compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfate and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect, as discussed above. Langer, *Science* 249: 1527, 1990 and Hanes, *Advanced Drug Delivery Reviews* 28: 97-119, 1997. The compositions and pharmacologic agents described herein can be administered in the form of a depot injection or implant preparation which can be formulated in such a manner as to permit a sustained or pulsatile release of the active ingredient.

Transdermal administration includes percutaneous absorption of the composition through the skin. Transdermal formulations include patches, ointments, creams, gels, salves and the like. Transdermal delivery can be achieved using a skin patch or using transferosomes. [Paul et al., *Eur. J. Immunol.* 25: 3521-24, 1995; Cevc et al., *Biochem. Biophys. Acta* 1368: 201-15, 1998].

"Treating" or "treatment" includes preventing or delaying the onset of the symptoms, complications, or biochemical indicia of a disease, alleviating or ameliorating the symptoms or arresting or inhibiting further development of the disease, condition, or disorder. A "patient" is a human subject in need of treatment.

An "effective amount" refers to that amount of the therapeutic agent that is sufficient to ameliorate of one or more symptoms of a disorder and/or prevent advancement of a disorder, cause regression of the disorder and/or to achieve a desired effect.

The words "a" or "an" are meant to encompass one or more, unless otherwise specified.

It is to be further understood that where descriptions of various embodiments use the term "comprising," those skilled in the art would understand that in some specific instances, an embodiment can be alternatively described using language "consisting essentially of" or "consisting of"

BAYBUTT, T. R., FLICKINGER, J. C., CAPAROSA, E. M. & SNOOK, A. E. (2019). Advances in chimeric antigen receptor T-Cell therapies for solid tumors. Clinical Pharmacology & Therapeutics, 105(1), 71-78.

CACCURI, F., GIAGULLI, C., BUGATTI, A., BENETTI, A., ALESSANDRI, G., RIBATTI, D., MARSICO, S., APOSTOLI, P., SLEVIN, M. A., RUSNATI, M., GUZMAN, C. A., FIORENTINI, S. & CARUSO, A. (2012). HIV-1 matrix protein p17 promotes angiogenesis via chemokine receptors CXCR1 and CXCR2. Proceedings of the Proc Natl Acad Sci USA, 109(36), 14580-14585.

CELADA, A., ALLEN, R., ESPARZA, I., GRAY, P. W. & SCHREIBER, R. D. (1985). Demonstration and partial characterization of the interferon-gamma-receptor on human mononuclear phagocytes. Journal of Clinical Investigation, 76(6), 2196-2205.

CZAJKOWSKY, D. M., HU, J., SHAO, Z. F. & PLEASS, R. J. (2012). Fc-fusion proteins: new developments and future perspectives. EMBO Molecular Medicine, 4(10), 1015-1028.

DE JONG, M. D., SIMMONS, C. P., THANH, T. T., HIEN, V. M., SMITH, G. J. D., CHAU, T. N. B., HOANG, D. M., CHAU, N. V. V., KHANH, T. H., DONG, V. C., QUI, P. T., VAN CAM, B., HA, D. Q., GUAN, Y., PEIRIS, J. S. M., CHINH, N. T., HIEN, T. T. & FARRAR, J. (2006). Fatal outcome of human influenza A (H5N1) is associated with high viral load and hypercytokinemia. Nature Medicine, 12(10), 1203-1207.

DRAZEN, J. M. C., R. L.; GOLDMAN, L.; BENNETT, C. (2000). Cecil textbook of medicine, 21st edition edition. Philadelphia: W. B. Saunders.

EBERHARDSON, M., KARLEN, P., LINTON, L., JONES, P., LINDBERG, A., KOSTALLA, M. J., LINDH, E., ODEN, A., GLISE, H. & WINQVIST, O. (2017). Randomised, double-blind, placebo-controlled trial of CCR9-targeted leukapheresis treatment of ulcerative colitis patients. Journal of Crohns & Colitis, 11(5), 534-542.

HU, Y., ZHANG, L., WU, R. R., HAN, R. F., JIA, Y. H., JIANG, Z. M., CHENG, M. X., GAN, J., TAO, X. & ZHANG, Q. P. (2011). Specific killing of CCR9 high-expressing acute T lymphocytic leukemia cells by CCL25 fused with PE38 toxin. Leukemia Research, 35(9), 1254-1260.

HUANG, C., WANG, Y. & LI, X. (2020). Clinical features of patients infected with 2019 novel coronavirus in Wuhan, China (vol 395, pg 497, 2020). Lancet, 395 (10223), 496-496.

ITTERSHAGEN, S., ERICSON, S., ELDJEROU, L., SHOJAEE, A., BLEICKARDT, E., PATEL, M., TARAN, T., ANAK, O., HALL, C., LEUNG, M., ROCCOBERTON, D., SALMON, F., FUCHS, M., ROMANOV, V. & LEBWOHL, D. (2019). Industry's giant leap into cellular therapy: catalyzing chimeric antigen receptor T cell (CAR-T) immunotherapy. Current Hematologic Malignancy Reports, 14(1), 47-55.

JAIN, M. D. & DAVILA, M. L. (2018). Concise Review: Emerging principles from the clinical application of chimeric antigen receptor t cell therapies for B cell malignancies. Stem Cells, 36(1), 36-44.

JERABEK-WILLEMSEN, M., ANDRE, T., WANNER, R., ROTH, H. M., DUHR, S., BAASKE, P. & BREITSPRECHER, D. (2014). MicroScale thermophoresis: interaction analysis and beyond. Journal of Molecular Structure, 1077, 101-113.

KWON, H. R. (2010). Study of the structure and function of CXC chemokine receptor 2. Master's Thesis, University of Tennessee.

LAPORTE, S. L., JUO, Z. S., VACLAVIKOVA, J., COLF, L. A., QI, X. L., HELLER, N. M., KEEGAN, A. D. & GARCIA, K. C. (2008). Molecular and structural basis of cytokine receptor pleiotropy in the interleukin-4/13 system. Cell, 132(2), 259-272.

MEKHAIEL, D. N. A., CZAJKOWSKY, D. M., ANDERSEN, J. T., SHI, J. G., EL-FAHAM, M., DOENHOFF, M., MCINTOSH, R. S., SANDLIE, I., HE, J. F., HU, J., SHAO, Z. F. & PLEASS, R. J. (2011). Polymeric human Fc-fusion proteins with modified effector functions. Scientific Reports, 1.

MIKULECKY, P., CERNY, J., BIEDERMANNOVA, L., PETROKOVA, H., KUCHAR, M., VONDRASEK, J., MALY, P., SEBO, P. & SCHNEIDER, B. (2013). Increasing affinity of interferon-gamma receptor 1 to interferon-gamma by computer-aided design. Biomed Research International.

QING, R., HAN, Q. Y., SKUHERSKY, M., CHUNG, H., BADR, M., SCHUBERT, T. & ZHANG, S. G. (2019). QTY code designed thermostable and water-soluble chimeric chemokine receptors with tunable ligand affinity. Proc Natl Acad Sci USA, 116(51), 25668-25676.

RAJARATHNAM, K., PRADO, G. N., FERNANDO, H., CLARK-LEWIS, I. & NAVARRO, J. (2006). Probing receptor binding activity of interleukin-8 dimer using a disulfide trap. Biochemistry, 45(25), 7882-7888.

RICHTER, D., MORAGA, I., WINKELMANN, H., BIRKHOLZ, O., WILMES, S., SCHULTE, M., KRAICH, M., KENNEWEG, H., BEUTEL, O., SELENSCHIK, P., PATEROK, D., GAVUTIS, M., SCHMIDT, T., GARCIA, K. C., MULLER, T. D. & PIEHLER, J. (2017). Ligand-induced type II interleukin-4 receptor dimers are sustained by rapid re-association within plasma membrane microcompartments. Nature Communications, 8, No. 15976.

SAVARIN, C. & BERGMANN, C. C. (2018). Fine Tuning the Cytokine Storm by IFN and IL-10 Following Neurotropic Coronavirus Encephalomyelitis. Frontiers in Immunology, 9, 3022.

SHIMABUKURO-VORNHAGEN, A., GODEL, P., SUBKLEWE, M., STEMMLER, H. J., SCHLOSSER, H. A., SCHLAAK, M., KOCHANEK, M., BOLL, B. & VON BERGWELT-BAILDON, M. S. (2018). Cytokine release syndrome. Journal for Immunotherapy of Cancer, 6 (1) 56.

SOMOVILLA-CRESPO, B., MONZON, M. T. M., VELA, M., CORRALIZA-GORJON, I., SANTAMARIA, S., GARCIA-SANZ, J. A. & KREMER, L. (2018). 92R monoclonal antibody inhibits human CCR9(+) leukemia cells growth in NSG mice xenografts. Frontiers in Immunology, 9.

SONNHAMMER, E. L., VON HEIJNE, G. & KROGH, A. (1998). A hidden Markov model for predicting transmembrane helices in protein sequences. In Ismb, vol. 6, pp. 175-182.

SRIVASTAVA, S. & RIDDELL, S. R. (2015). Engineering CAR-T cells: Design concepts. Trends in Immunology, 36(8), 494-502.

TAN, J. C., INDELICATO, S. R., NARULA, S. K., ZAVODNY, P. J. & CHOU, C. C. (1993). Characterization of interleukin-10 receptors on human and mouse cells. J. Biological Chemistry, 268(28), 21053-21059.

TISONCIK, J. R., KORTH, M. J., SIMMONS, C. P., FARRAR, J., MARTIN, T. R. & KATZE, M. G. (2012). Into the eye of the cytokine storm. Microbiology and Molecular Biology Reviews, 76(1), 16-32.

TU, Z. B., XIAO, R. J., XIONG, J., TEMBO, K. M., DENG, X. Z., XIONG, M., LIU, P., WANG, M. & ZHANG, Q. P. (2016). CCR9 in cancer: oncogenic role and therapeutic targeting. J. Hematology & Oncology, 9:10 doi: 10.1186/s13045-016-0236-7.

XU, X. J. & TANG, Y. M. (2014). Cytokine release syndrome in cancer immunotherapy with chimeric antigen receptor engineered T cells. Cancer Letters, 343(2), 172-178.

XU, Z., SHI, L., WANG, Y., ZHANG, J., HUANG, L., ZHANG, C., LIU, S., ZHAO, P., LIU, H. & ZHU, L. (2020). Pathological findings of COVID-19 associated with acute respiratory distress syndrome. The Lancet Respiratory Medicine. pii: S2213-2600(20)30076-X. doi: 10.1016/S2213-2600(20)30076-X.

ZHANG, S. G., TAO, F., QING, R., TANG, H. Z., SKUHERSKY, M., CORIN, K., TEGLER, L., WASSIE, A., WASSIE, B., KWON, Y., SUTER, B., ENTZIAN, C.,

SCHUBERT, T., YANG, G., LABAHN, J., KUBICEK, J. & MAERTENS, B. (2018). QTY code enables design of detergent-free chemokine receptors that retain ligand-binding activities. Proc Natl Acad Sci USA, 115(37), E8652-E8659.

All documents and references described herein are individually incorporated by reference to into this document to the same extent as if there were written in this document in full or in part.

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

While this invention has been particularly shown and described with references to preferred embodiments thereof, it will be understood by those skilled in the art that various changes in form and details may be made therein without departing from the scope of the invention encompassed by the appended claims.

What is claimed is:

1. A Fc fusion receptor protein comprising an Fc domain, one or more ligand binding domains and a QTY transmembrane domain, wherein the ligand-binding domain is an extracellular domain of human interleukin-4 receptor subunit alpha comprising SEQ ID NO. 9, and the QTY transmembrane domain comprises SEQ ID NO. 4.

2. The Fc fusion of receptor protein of claim 1, wherein the Fc domain comprises a human immunoglobulin constant region.

3. The Fc fusion of receptor protein of claim 1, wherein the Fc domain comprises an IgG constant domain.

4. The Fc fusion of receptor protein of claim 1, wherein the Fc Domain is fused to the QTY transmembrane domain via a hinge region.

5. The Fc fusion of receptor protein of claim 1, wherein comprising two identical ligand binding domains.

6. The Fc fusion of receptor protein of claim 1, wherein each ligand binding domain is directly bound to a QTY transmembrane domain.

7. A pharmaceutical composition comprising the Fc fusion receptor protein of claim 1 and a pharmaceutically acceptable carrier.

* * * * *